(12) United States Patent
Amshey et al.

(10) Patent No.: US 7,850,835 B2
(45) Date of Patent: Dec. 14, 2010

(54) SOLUTION PHASE ELECTROPHORESIS DEVICE, COMPONENTS, AND METHODS

(75) Inventors: Joseph W. Amshey, Encinitas, CA (US); Timothy V. Updyke, Temecula, CA (US); Thomas R. Jackson, La Jolla, CA (US); Michael Thacker, San Diego, CA (US)

(73) Assignee: Life Technologies Corporation, Carlsbad, CA (US)

( * ) Notice: Subject to any disclaimer, the term of this patent is extended or adjusted under 35 U.S.C. 154(b) by 904 days.

(21) Appl. No.: 10/843,526

(22) Filed: May 10, 2004

(65) Prior Publication Data

US 2005/0006239 A1  Jan. 13, 2005

Related U.S. Application Data

(60) Provisional application No. 60/469,538, filed on May 9, 2003, provisional application No. 60/471,390, filed on May 16, 2003.

(51) Int. Cl.
*G01N 27/00* (2006.01)
*B01D 61/00* (2006.01)

(52) U.S. Cl. .................. 204/644; 204/518; 204/548; 204/627

(58) Field of Classification Search ......... 204/518–544, 204/627–640, 548, 644
See application file for complete search history.

(56) References Cited

U.S. PATENT DOCUMENTS

| | | | |
|---|---|---|---|
| 3,844,925 A * | 10/1974 | Stathakos | 204/610 |
| 4,130,470 A * | 12/1978 | Rosengren et al. | 204/451 |
| 4,204,929 A * | 5/1980 | Bier | 204/518 |
| 4,243,507 A | 1/1981 | Martin et al. | |
| 4,401,538 A | 8/1983 | Hausfeld | |
| 4,608,147 A | 8/1986 | Clad | |
| 4,673,483 A | 6/1987 | Mandle | |
| 4,691,820 A | 9/1987 | Martinez | |
| 4,925,545 A | 5/1990 | Murel | |
| 4,971,670 A | 11/1990 | Faupel et al. | |
| 5,039,386 A | 8/1991 | Margolis | |
| 5,082,548 A | 1/1992 | Faupel et al. | |
| 5,126,026 A * | 6/1992 | Chlanda | 204/522 |
| 5,133,862 A | 7/1992 | Cannan et al. | |
| 5,225,080 A | 7/1993 | Karbachsch et al. | |
| 5,336,387 A | 8/1994 | Egen et al. | |
| 5,540,826 A | 7/1996 | Bier et al. | |
| 5,578,180 A | 11/1996 | Engelhorn et al. | |
| 5,773,645 A | 6/1998 | Mochstrasser | |
| 5,851,390 A | 12/1998 | Lemonnier | |
| 5,891,328 A * | 4/1999 | Goldstein | 210/321.6 |

(Continued)

FOREIGN PATENT DOCUMENTS

WO  WO 92/00795  1/1992

(Continued)

OTHER PUBLICATIONS

Photo of Sitodiplosis mosellana (Géhin), wheat midge eggs, from http://esc-sec.org/photo_archive/photo_archive5.htm.*

(Continued)

*Primary Examiner*—Jeffrey T. Barton

(57) ABSTRACT

A device for fluid phase electrophoresis, particularly solution phase isoelectric focusing, components thereof, and methods for use are presented.

30 Claims, 20 Drawing Sheets

U.S. PATENT DOCUMENTS

| | | | |
|---|---|---|---|
| 5,922,185 A | | 7/1999 | Updyke et al. |
| 5,928,488 A | * | 7/1999 | Newman .................... 205/510 |
| 6,059,948 A | | 5/2000 | Updyke et al. |
| 6,096,182 A | | 8/2000 | Updyke et al. |
| 6,129,828 A | | 10/2000 | Sheldon, III et al. |
| 6,143,154 A | | 11/2000 | Updyke et al. |
| 6,156,182 A | | 12/2000 | Olech |
| 6,162,338 A | | 12/2000 | Updyke et al. |
| 6,171,466 B1 | | 1/2001 | Rhodes et al. |
| 6,485,544 B1 | | 11/2002 | Ziske |
| 6,521,111 B1 | | 2/2003 | Amshey et al. |
| 6,638,408 B1 | * | 10/2003 | Speicher et al. ............. 204/458 |
| 6,770,203 B2 | | 8/2004 | Leoncavallo et al. |
| 7,361,260 B2 | | 4/2008 | Amshey et al. |
| 7,622,028 B2 | | 11/2009 | Amshey et al. |
| 2003/0019753 A1 | * | 1/2003 | Ogle et al. .................. 204/548 |
| 2004/0031683 A1 | | 2/2004 | Hammermann et al. |

FOREIGN PATENT DOCUMENTS

| | | |
|---|---|---|
| WO | WO 00/17631 | 3/2000 |
| WO | WO 01/36449 | 5/2001 |
| WO | WO 01/75432 | 10/2001 |
| WO | WO 01/77655 | 10/2001 |
| WO | WO 03/008977 | 1/2003 |

OTHER PUBLICATIONS

Photo of *Sitodiplosis mosellana* (Gehin), wheat midge eggs, from http://esc-sec.org/photo_archive/photo_archive5.htm. Printed Aug. 5, 2005.*

Ali-Khan et al., "Overview of Proteome Analysis", Current Protocols in Protein Science 22.1:1-19 (2002).

Bellini et al., "Synthesis of Zwitterionic Acrylic Acid Buffers for Isoelectric Focusing in Immobilized pH Gradients", Electrophoresis, 19:1590-1595 (1998).

Charlionet et al., "Easy "home-made" Immobilized pH Gradients for Isoelectric Focusing", Electrophoresis, 5:176-178 (1984).

Choe et al., "A Comparison of Three Commercially Available Isoelectric Focusing Units for Proteome Analysis: The Multiphor, the IPGphor and the Protean IEF Cell", Electrophoresis, 21:993-1000 (2000).

Corthals et al., "The Dynamic Range of Protein Expression: A Challenge for Proteomic Research", Electrophoresis, 21(6):1104-1115 (2000).

Corthals et al., 'Prefractionation of Protein Samples Prior to Two-dimensional Electrophoresis', Electrophoresis 1997, vol. 18, pp. 317-323.

Dutt et al., "Proteomic Analysis", Biochemical Engineering, 176-179.

Gygi et al., "Evaluation of Two-Dimensional Gel Electrophoresis-based Proteome Analysis Technology", PNAS, 97(17):9390-9395 (2000).

Harvard/Amika ElectroPrep, N117-N120.

Herbert et al., "A Turning Point in Proteome Analysis: Sample Prefractionation via multicompartment Electrolyzers with Isoelectric Membranes", Electrophoresis, 21:3639- 3648 (2000).

Hille et al., "Possibilities to Improve Automation, Speed and Precision of Proteome Analysis: A comparison of two-dimensional electrophoresis and alternatives", Electrophoresis, 22:4035-4052 (2001).

Hochstrasser, et al., Preparative isoelectrofocusing and high resolution 2-dimensional gel electrophoresis for concentration and purification of proteins, Appl and Theo Electrophoresis (1991), 1, 333-337.

Hoefer, "IsoPrime IEF Purification Unit User Manual", P18-IM Rev E2-99.

Hoefer, "IsoPrime Multi-Chambered Electrofocusing Unit", Pharmacia Biotech, P18-93-07.

Issaq et al., "Methods for Fractionation, Separation and Profiling of Proteins and Peptides", Electrophoresis, 23:3048-3061 (2002).

Issaq, "The Role of Separation Science in Proteomics Research", Electrophoresis, 22:3629-3638 (2001).

MacBeath, "Protein Microarrays and Proteomics", Nature Genetics Supplement, 32:526-532 (2002).

Ouadroni et al., 'Proteomics and automation', Electrophoresis 1999, 20:664-677.

Rabilloud, "Two-Dimensional Gel Electrophoresis in Proteomics: Old, old fashioned, but it still climbs up the mountains", Proteomics, 2:3-10 (2002).

Rabilloud, "Solubilization of Proteins in 2-D Electrophoresis", Methods in Molecular Biology, 112:9-19 (1999).

Righetti et al., "Prefraction Techniques in Proteome Analysis", Analytical Chemistry, (Jun. 1, 2001).

Righetti et al, "Preparative Purification of Human Monoclonal Antibody Isoforms in a Multi-Compartment Electrolyser with Immobiline Membranes", Journal of Chromatography, 500:681-696 (1990).

Righetti et al., "Preparative Protein Purification in a Multi-Compartment Electrolyser with Immobiline Membranes", Journal of Chromotography, vol. 475: 293-309 (1989).

Rotofor System Instruction Mannual, Rio-Rad.

Sanchez, "Sample Preparation and Solubilization: crucial steps preceding the two-dimensional gel electrophoresis process", Geneva University Hospital, Switzerland (1998).

Speicher, "Gel-Based Proteome Analysis", Current Protocols in Protein Science, 22.01- 22.02 (2003).

Tan et al., "A Miniaturized Multichamber Solution Isoelectric Focusing Device for Separation of Protein Digests", Electrophoresis, 23:3599-3607 (2002).

Zuo et al., "A Method for Global Analysis of Complex Proteomes Using Sample Prefractionation by Solution Isoelectrofocusing Prior to Two-Dimensional Electrophoresis", Analytical Biochemistry, 284:266-278 (2000).

Zuo et al., "Towards Global Analysis of Mammalian Proteomes Using Sample Prefractionation Prior to Narrow pH Range Two-Dimensional Gels and Using One-Dimensional Gels for Insoluble and Large Proteins", Electrophoresis, 22:1603-1615 (2001).

Zuo et al., "Enhanced Analysis of Human Breast Cancer Proteomes Using Micro-Scale Solution Isoelectrofocusing Combined with High Resolution 1-D and 2-D Gels", Journal of Chromatography B, 782:253-265 (2002).

Zuo et at, "Comprehensive Analysis of Complex Proteomes Using Microscale Solution Isoelectrofocusing Prior to Narrow pH Range Two-Dimensional Electrophoresis", Proteomics, 2:58-68 (2002).*

Zuo et al., "Microscale Solution Isoelectrofocusing: A Sample Prefractionation Method For Comprehensive Proteome Analysis", Methods in Molecular Biology, 244:361-375 (2004).*

Office Action mailed May 14, 2008 in U.S. Appl. No. 10/895,427.

Office Action mailed Aug. 20, 2007 in U.S. Appl. No. 10/895,427.

Office Action mailed Jul. 13, 2009 in U.S. Appl. No. 10/895,427.

Response to Office Action mailed Aug. 20, 2007 in U.S. Appl. No. 10/895,427.

Response to Non Final Rejection mailed Feb. 20, 2008 in U.S. Appl. No. 10/895,427.

International Search Report issued Dec. 17, 2004 in WO 2004/104548.

* cited by examiner

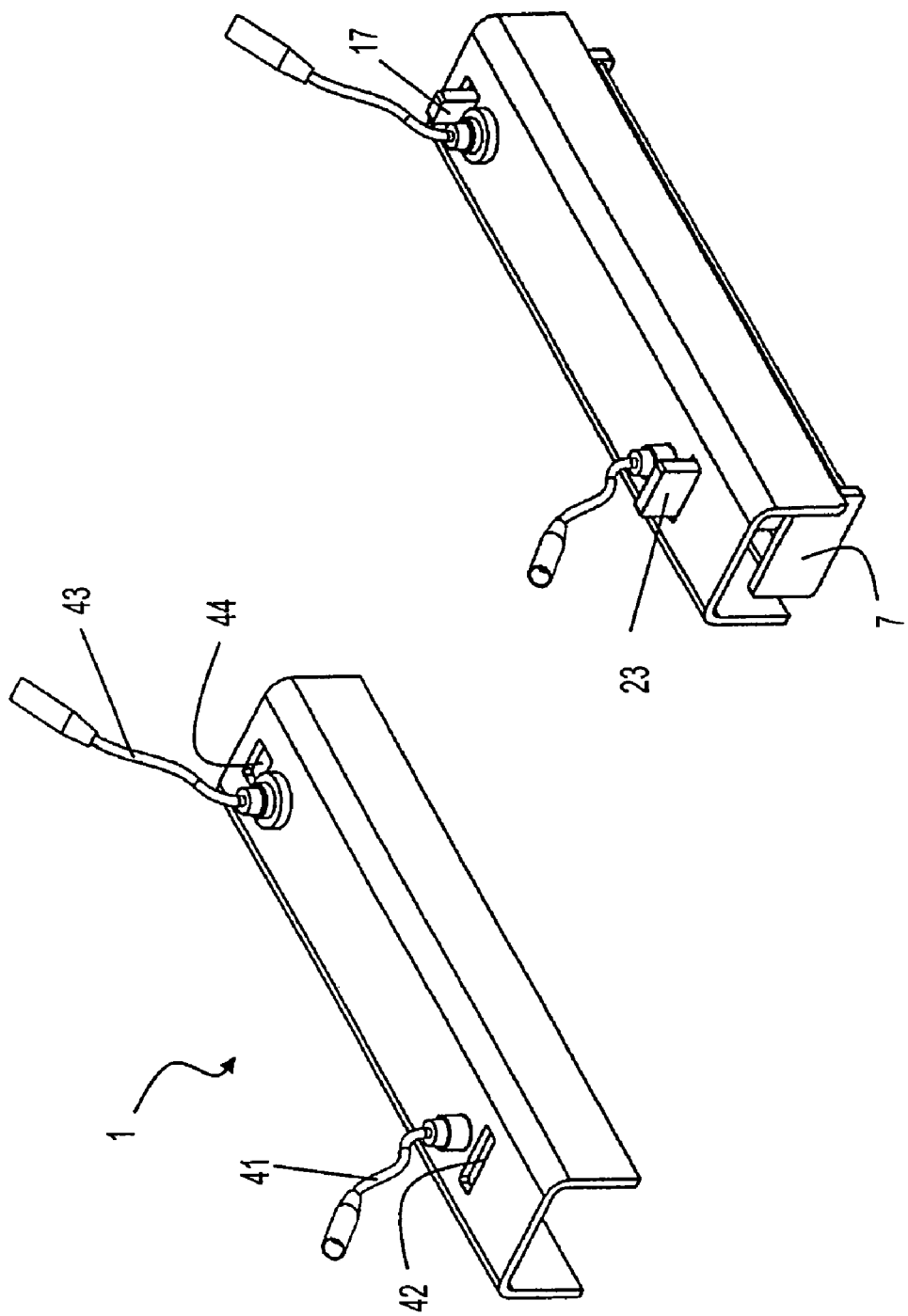

SOLUTION PHASE ELECTROPHORESIS DEVICE, COMPONENTS, AND METHODS

FIELD OF THE INVENTION

The present invention is in the field of devices, components, and methods for electrophoresis, particularly isoelectric focusing, more particularly solution phase isoelectric focusing (IEF).

BACKGROUND OF THE INVENTION

The complexity of eukaryotic proteomes—that is, the total number of distinct protein species present concurrently in a eukaryotic cell, including alternatively spliced isoforms and variants differing in post-translational modification—typically exceeds the resolving capacity of current analytical techniques.

For example, the number of distinct protein species in eukaryotic cells typically far exceeds the spatial resolution of two-dimensional polyacrylamide gel electrophoresis (2D PAGE) gels, with large numbers of distinct protein species appearing to comigrate. The limited spatial resolution in turn constrains the dynamic detection range of the technique: efforts to observe low abundance species by increasing the initial protein load lead to increased obscuration by high abundance species.

Recently, efforts have been made to increase resolution of such protein analytical techniques by prefractionating the protein mixture prior to analysis. In one approach, complex mixtures are prefractionated using solution phase isoelectric focusing, yielding fractions having distinct pI ranges that can thereafter be separately analyzed by 2D PAGE with increased resolution. See Zuo and Speicher, Anal. Biochem. 284:266-278 (2000); Zuo et al., Electrophoresis 22:1603-1615 (2001); Zuo and Speicher, Proteomics 2:58-68 (2002); Ali-Khan et al., Current Protocols in Protein Science 22.1:1-19 (2002); Zuo et al., J. Chromatography B 782:253-265 (2002); and Wistar Institute, WO 01/75432, the disclosures of which are incorporated herein by reference in their entireties. See also Tan et al., Electrophoresis 23:3599-3607 (2002); WO 01/36449; WO 00/17631; and Righetti et al., J. Chromatography 475:293-309 (1989).

A number of devices capable of solution phase isoelectric focusing are available commercially. None of the devices, however, provides particularly convenient solution phase IEF prefractionation of small volume protein samples with a simple device in a format that readily interfaces with subsequent analytical techniques such as 2D PAGE.

There thus exists a continuing need in the art for devices, components, and methods for solution phase electrophoresis, particularly solution phase isoelectric focusing.

SUMMARY OF THE INVENTION

The present invention satisfies these and other needs in the art by providing a solution phase isoelectric focusing device that is assembled by simply inserting components (e.g., chambers) into a loading tube and holding them in place with a single screw cap. The screw cap is tightened to ensure leak-proof seals between the chambers and other component parts. The device is easy to disassemble by simply sliding the chambers and other components out of the loading tube. In preferred embodiments, air bubbles are avoided in sample chambers by using optional specially shaped openings and cap seals to seal the chambers after loading and/or during electrophoresis or subsequent manipulations.

Generally, in IEF applications, the device uses fixed pH membrane disks. Such disks can have a shape that limits the electrodecantation of proteins. The shape of the membrane disks can also be used to properly orientate a disk in position between two chambers, thus minimizing or eliminating leaks that arise from poorly orientated disks. Disk shapes that have these and other desirable aspects are disclosed herein.

In one aspect, the invention relates to devices for IEF. In some embodiments, the device does not require means for sample recirculation, mixing or other agitation within its chambers during the electrophoretic separation. In other embodiments, however, the device is positioned on a rocker platform or a rotary platform to move the entire device during operation, thus effecting sample agitation.

In another embodiment, the invention relates to IEF devices having a loading tube into which a plurality of sample chambers is loaded. The tube aligns the sample chambers in a coaxial orientation during assembly and operation. The chambers may be compressed using one or more actuators, such as a screw cap at one end of the loading tube.

Thus, in some embodiments, sample chambers are held tightly in position by a screw cap at one end of the loading tube. The screw cap compresses the chambers against one another as it is tightened. Sealing O-rings between the chambers compress under the pressure to form leak-proof seals.

In further embodiments, an anode end piece is introduced to the loading tube before the first sample chamber to facilitate subsequent disassembly of the device. The anode end piece has a protrusion that slides along a channel in the loading tube, facilitating removal of chambers from the loading tube.

In yet further embodiments, the electrode wires, which are submerged in electrode buffer during use, are housed in circumferential detents in cylindrical electrode plugs. The recessed electrode wires are protected from damage during use and during cleaning. The electrode plugs are optionally removable from the device for cleaning, repair or replacement. Preferably, the electrodes provide for a more consistent electrical field regardless of support structure rotational orientation.

In yet further embodiments, the sample chambers have loading ports and corresponding cap seals having a design such that air is not trapped in sample chambers when they are sealed. A cap seal of the invention does not completely block the fill port until the cap seal is fully inserted, so that no air is trapped in closing the sample chambers.

Moreover, the present invention relates generally to methods and designs for sealing sample chambers without trapping air bubbles, wherein air is displaced from sample chambers by slightly over-filling the sample chamber with a supernatant fluid, and the excess of such fluid is displaced as the cap seal is inserted into the loading port. Such methods and cap seals can be used in other applications, both in those involving aqueous solutions, as well as other liquids. Other liquids include without limitation organic solvents (e.g., benzene, other aromatic hydrocarbons, chlorinated hydrocarbons, hexane, dichloromethane, alcohols, ketones, ethers, amines, esters, petroleum products (oil, gas, etc.), paints, primers, sealants, liquefied gases (e.g., liquid oxygen, liquid nitrogen, etc.), culture media (i.e., for anaerobic bacteria) and the like. In general, this aspect of the invention applies to any liquid container the use of which would be enhanced by reduced contact with air and/or fewer air bubbles.

In another aspect, the present invention relates to immobilized buffer membranes for use in isoelectric focusing in one or more other embodiments of the invention.

In a further aspect, the invention relates to kits for solution IEF comprising the disks of the invention. Optionally, such kits further comprise one or more buffers, one or more sets of instruction, one or more protein standards, and/or one or more control samples.

In a further aspect, the invention relates to methods of separating, fractionating and characterizing proteins and other biomolecules using a device of the invention. Such processes involve electrophoresis, including without limitation isoelectric focusing (IEF).

BRIEF DESCRIPTION OF THE DRAWINGS

These and other objects and advantages of the present invention will be apparent upon consideration of the following detailed description, taken in conjunction with the accompanying drawings, in which like graphical representations and like characters refer to like structures throughout, and in which the terms "proximal" and "distal" refer to the position of a component relative to the anode when the device of the present invention is assembled and ready for use.

FIG. 9A is a proximal perspective view (from above) of a lid and associated anode and cathode cables, according to one embodiment of the present invention. Also shown are the anode and cathode tab slots of the lid.

FIG. 9B is a proximal perspective view (from above) of the lid and associated electrode cables of FIG. 9A, assembled with additional components of an embodiment of a device according to the present invention. In the embodiment shown, the cathode tab slot of the lid is shaped to receive only the cathode tab of the device, thus preventing the lid from being assembled with the device except in the orientation shown.

FIG. 12A is obtained with unfractionated lysate. Each of FIGS. 12B-12F is obtained using a fraction from a different one of the device sample chambers; the pH range of the device sample chamber is shown in large type below the IPG strip pH range.

FIG. 13A is obtained from the pI 4.6-5.4 lysate fraction using a pH 4-7 IPG strip, FIG. 13B from the pI 4.6-5.4 lysate fraction using a pH 4.5-5.5 narrow range IPG strip, with FIG. 13C showing an enlargement of the indicated region of the gel shown in FIG. 13B. FIG. 13D is obtained from unfractionated rat liver lysate using a pH 4.5-5.5 IPG strip, with FIG. 13E showing an enlargement of the indicated region of the gel shown in FIG. 13D.

FIG. 14A is a top perspective schematic view of the plug, without the electrode wire, particularly indicating the outlet for traversal of the wire from the plug interior to its exterior, and the circumferential detent near the plug bottom, around which the electrode wire wraps. FIG. 14B shows the plug of FIG. 14A with the electrode wire passing from the electrode, through the plug interior, through the outlet, and around the circumferential detent.

DETAILED DESCRIPTION OF THE INVENTION

In a first aspect, the invention provides a device, and components thereof, for solution phase electrophoretic separation of analytes within a sample.

The device comprises an anode, a cathode, a chamber stack disposed between the anode and cathode, and chamber stacking means.

As will be more fully described herein below, the chamber stack comprises a plurality of detachable sample chambers aligned along the electrical axis between the anode and cathode. The lumens of the coaxially aligned sample chambers are collectively capable of defining an electrically-conductive fluid column through the chamber stack.

The chamber stack further comprises a plurality of junctional partitions, each of the partitions positioned at a different one of the junctions between adjacent sample chambers. The partitions prevent bulk fluid flow between the chambers that are separated by the partitions. The partitions are permeable to small ions, however, and permeable to at least a plurality of the analytes in the sample, permitting both ion and at least some analyte flow therethrough.

The chamber stacking means is disposed completely external to the chamber stack. The stacking means facilitates the assembly of the chamber stack prior to electrophoresis and, during use, helps maintain the fluid integrity of the chamber stack.

Figure 1:
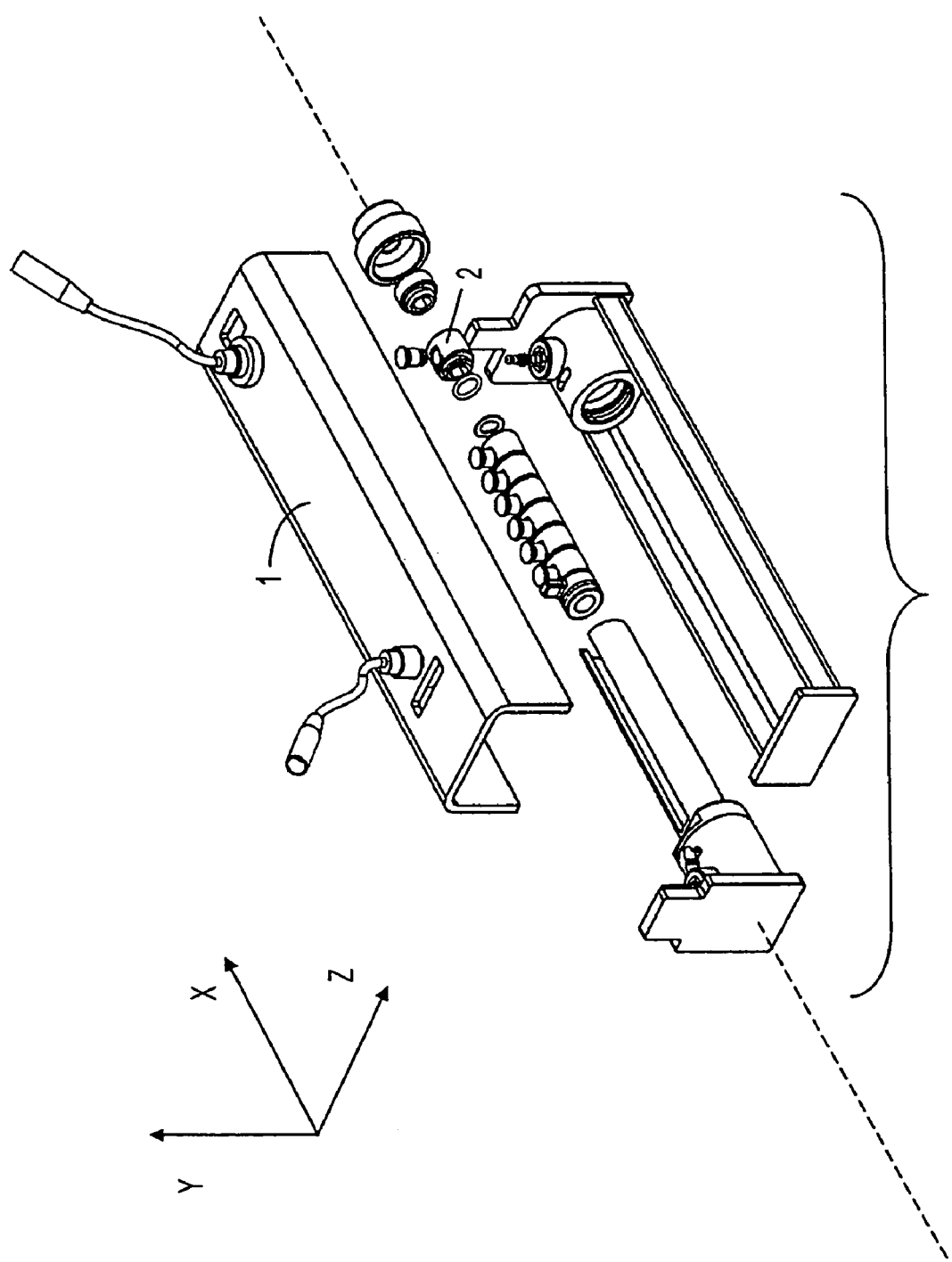
FIG. 1 is a partially exploded proximal perspective view (from above) of one embodiment of the device of the present invention.

A schematic depiction of an embodiment of the device of the present invention is presented in FIG. 1.

The various components, including lid 1, are viewed from a perspective above the proximal end of the partially disassembled device. As used herein, the terms "proximal" and "distal" refer to the position of a component relative to the anode when the device of the present invention is assembled and ready for use.

The embodiment shown in FIG. 1 shows seven sample chambers 2, but the number of sample chambers can be two, three, four, five, six, seven, eight, nine, ten or more, and still be within the scope of the present invention.

Figure 2A:
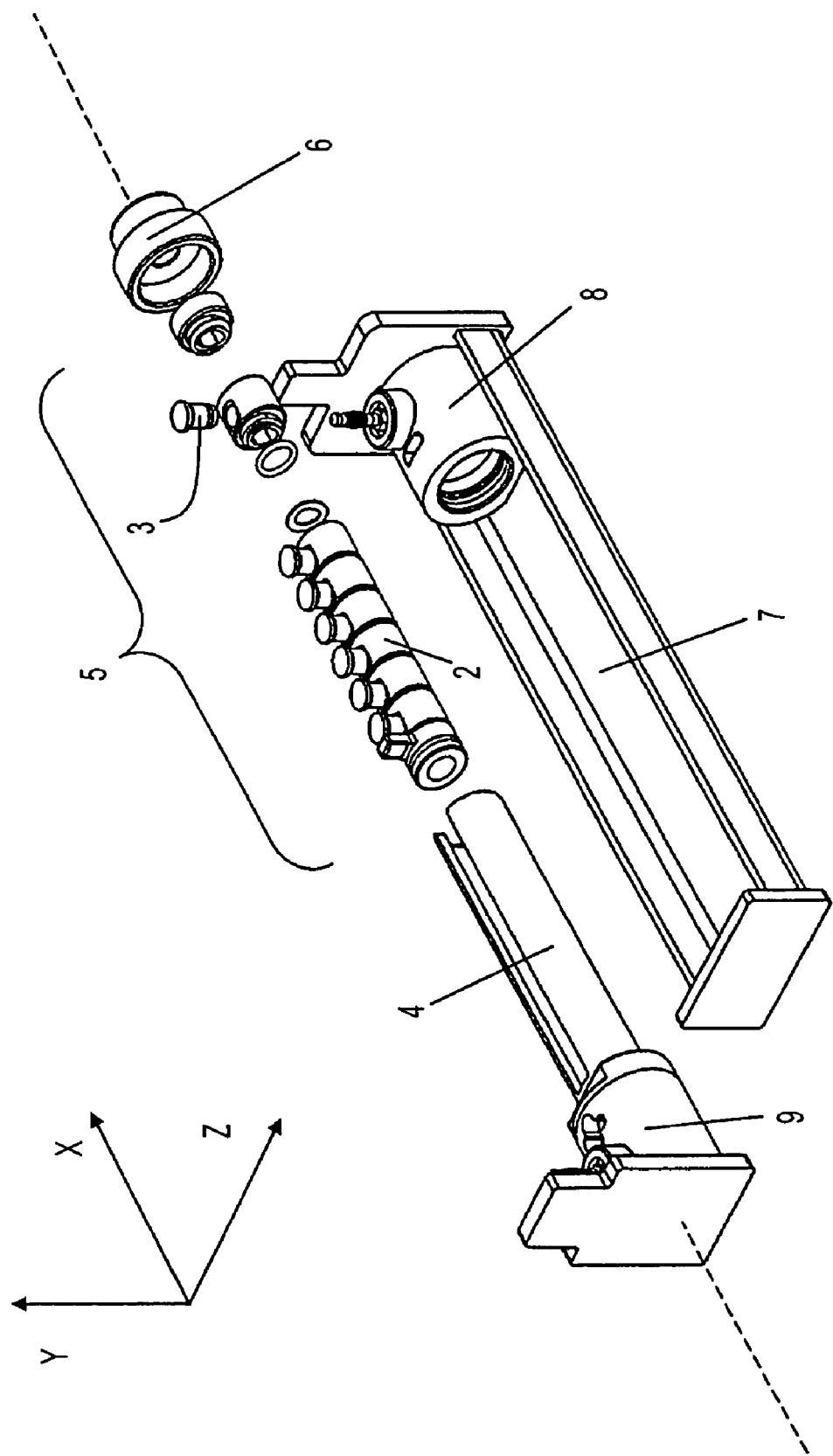
FIG. 2A is a partially exploded proximal perspective view (from above) of one embodiment of the device of the present invention, without the lid shown in FIG. 1.

FIG. 2A shows several components of the device of FIG. 1 at greater magnification. The lid is omitted for clarity.

In the embodiment shown, cathode buffer chamber 8 is integral with spill trough 7, and anode buffer chamber 9 is integral with loading tube 4. Such integral manufacture is not required, however, and either or both of chambers 8 and 9 may be discrete components; when discrete, either or both of chambers 8 and 9 may be capable of resting within, or being engaged to or engaged within, spill trough 7, or in other embodiments configured to rest upon a flat surface.

In yet other embodiments, the electrical axis may be vertical during operation. In such embodiments, cathode buffer chamber 8 may be integral with spill trough 7 and anode buffer chamber may be integral with loading tube 4, or either or both such chambers may be discrete components.

During electrophoresis, such as solution phase isoelectric focusing, sample chambers 2 are maintained in a coaxial orientation within loading tube 4. The chambers and other components that are inserted into loading tube 4 during electrophoresis (described in more detail below), are referred to collectively as the chamber stack 5. Chambers 2 are typically sealed during electrophoresis with cap seals 3. During electrophoresis, chamber stack 5 is held in place within the loading tube 4 by the screw cap 6, which applies a circumferentially uniform, proximally-directed, axial pressure on the chamber stack 5.

Once the chamber stack 5 is secured in the loading tube 4 by screw cap 6, the loading tube is lowered into the spill trough 7 and the distal end of screw cap 6 sealably engaged to the cathode buffer chamber 8.

Figure 2B:
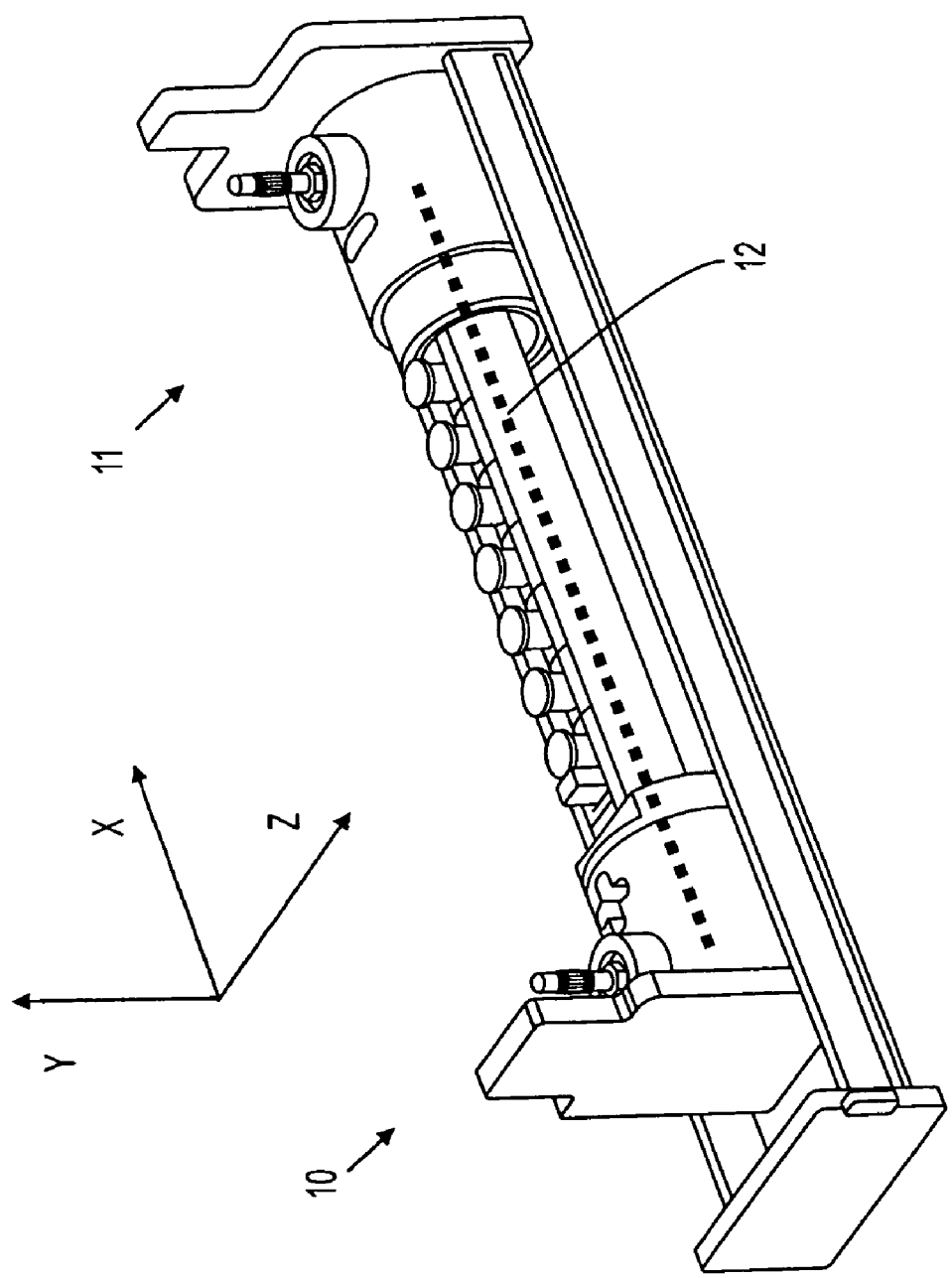
FIG. 2B is a proximal perspective view (from above) of the components shown in FIG. 2A, fully assembled. The axis of the electrical field is indicated by a dashed line.

FIG. 2B shows the components of FIG. 2A fully assembled.

The axis of the electric field 12 present during electrophoresis defines the axis along which the sample chambers are commonly aligned. The axis is defined by a line linking the submerged cathode and the submerged anode (further described below), and is shown by the bold dashed line in FIG. 2B.

Figure 3B:
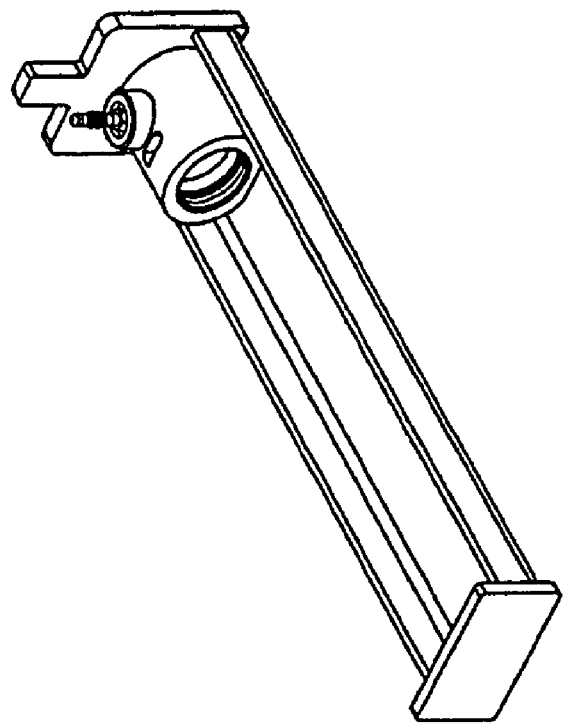
FIG. 3B is a proximal perspective view (from above) of the cathode buffer chamber and the spill trough of an embodiment of the device of the present invention, with the cathode electrode plug operationally engaged in the cathode port.
Figure 3A:
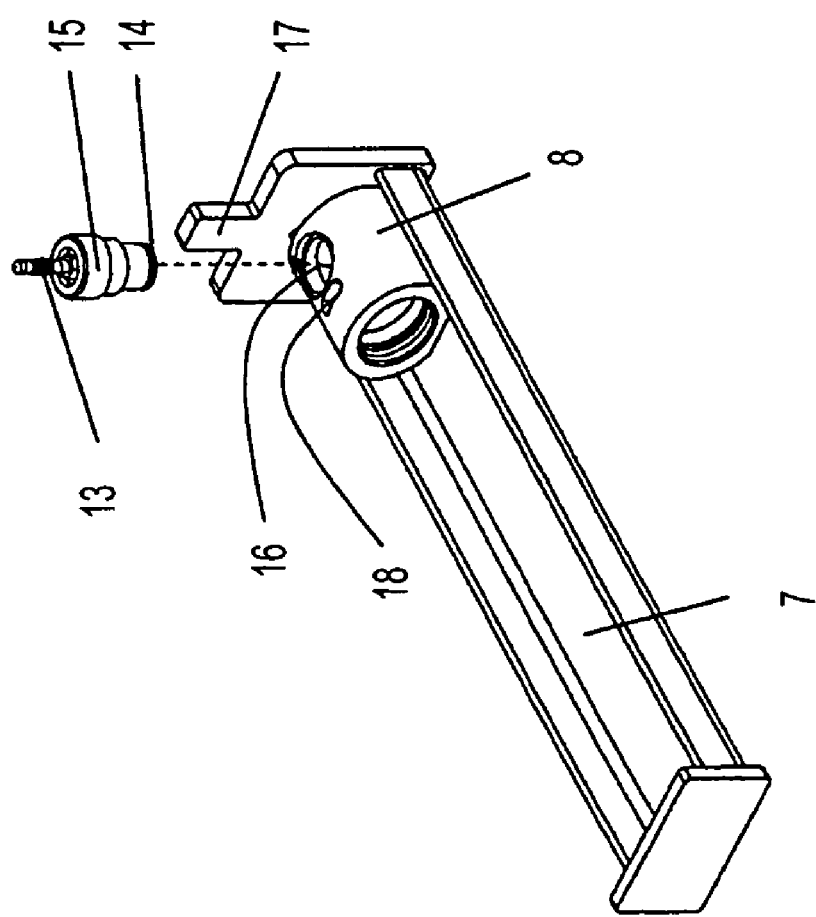
FIG. 3A is an exploded proximal perspective view (from above) of the cathode buffer chamber and the spill trough of an embodiment of the device of the present invention, with the cathode electrode plug disassembled from the cathode buffer chamber.

FIG. 3A shows the spill trough 7 and various components of the cathode region of the device shown in FIG. 1.

In the embodiment shown, spill trough 7 provides a reservoir to catch any electrophoresis buffer that might leak, a useful safety feature, and also provides underlying structural support for other components of the device. Spill trough 7 is optional, however, and is omitted in other embodiments. As would be apparent, in these latter embodiments, cathode buffer chamber 8 is designed to be a discrete component separate from the spill trough.

With further reference to FIG. 3A, cathode plug 15 is the component housing both the cathode electrode 13 and the cathode wire 14.

Cathode electrode 13 is the point of electrical contact of the device with the negative terminal of an external power supply (not shown). Cathode electrode 13 is in electrical contact with cathode wire 14. In the embodiment shown, cathode wire 14 extends from the cathode electrode through the interior of cathode plug 15.

In other embodiments, cathode wire 14 is routed down the outside of cathode plug 15. Routing cathode wire 14 through the interior of cathode plug 15 presents certain advantages, however. For example, if cathode plug 15 is made of an insulative material, routing the conductive wire inside the insulative material reduces or eliminates off-axis line charge, which could cause an asymmetrical field.

As shown in FIG. 3B, cathode plug 15 is engaged for use within cathode port 16, thus bringing cathode wire 14 into contact with the interior of buffer chamber 8.

In some embodiments, such as those shown in FIGS. 3A and 3B, cathode plug 15 is removably engageable with the cathode buffer chamber. By removably engageable is meant that the user can remove and replace it in the cathode port without damaging the device.

In such embodiments, cathode plug 15 is inserted prior to use into cathode port 16, as shown in FIG. 3B. In one such embodiment, cathode plug 15 simply rests in the cathode port 16. In another embodiment, cathode plug 15 snaps into the cathode port 16. In yet another embodiment, the cathode plug 15 screws into the cathode port 16.

In certain removable plug embodiments, cathode plug 15 is integral with or removably engaged with the lid 1, and is inserted into cathode port 16 when lid 1 is engaged with cathode tab 17 and anode tab 23 (further described below).

In alternative embodiments, cathode plug 15 is permanently or semi-permanently sealed within the cathode port 16, and may even be integral therewith.

The nature of the connection between the cathode plug and the cathode port can vary but still be within the scope of the invention.

The cathode buffer chamber 8 is located at the distal end of the spill trough 7. The cathode buffer chamber 8 is filled during operation (i.e., during electrophoresis) with an electrically conductive cathode buffer which provides electrical connectivity between the cathode wire 14 and the lumen of chamber stack 5 within the loading tube 4.

The cathode buffer chamber 8 optionally further comprises a cathode buffer inlet 18 (see FIG. 3A) for the introduction (or removal) of cathode buffer. The cathode buffer inlet 18 may optionally have a shape distinguishable from the anode buffer inlet (shown and discussed herein) to ensure the user does not introduce the wrong buffer into the cathode buffer chamber 8. In the embodiment shown in FIGS. 3A and 3B, the cathode buffer inlet 18 is shaped like a "minus sign" (−). Such identifying indicia may, in addition or in the alternative, be present elsewhere on cathode buffer chamber 8.

In certain embodiments, cathode buffer chamber 8 is transparent, permitting direct visualization of dyes capable of migrating to the cathode during electrophoresis.

Cathode buffer chamber 8 may usefully be designed to have a volume of 10 ml, 15 ml, even 16 ml, 17 ml, 18 ml, 19 ml, or 20 ml or more.

Spill trough 7 may also comprise a cathode tab 17 suited to fit through the cathode tab slot 44 in lid 1 when the device is fully assembled (see FIGS. 9A and 9B and description below). The size and/or shape of the cathode tab 17 may optionally be distinct from the size and/or shape of the anode tab (discussed herein below) to ensure that the lid, and thus the electrode cables, may only be attached with the proper polarity. In the embodiment shown in FIGS. 2A and 2B, cathode tab 17 is narrower (shorter) than anode tab 23.

Figure 4B:
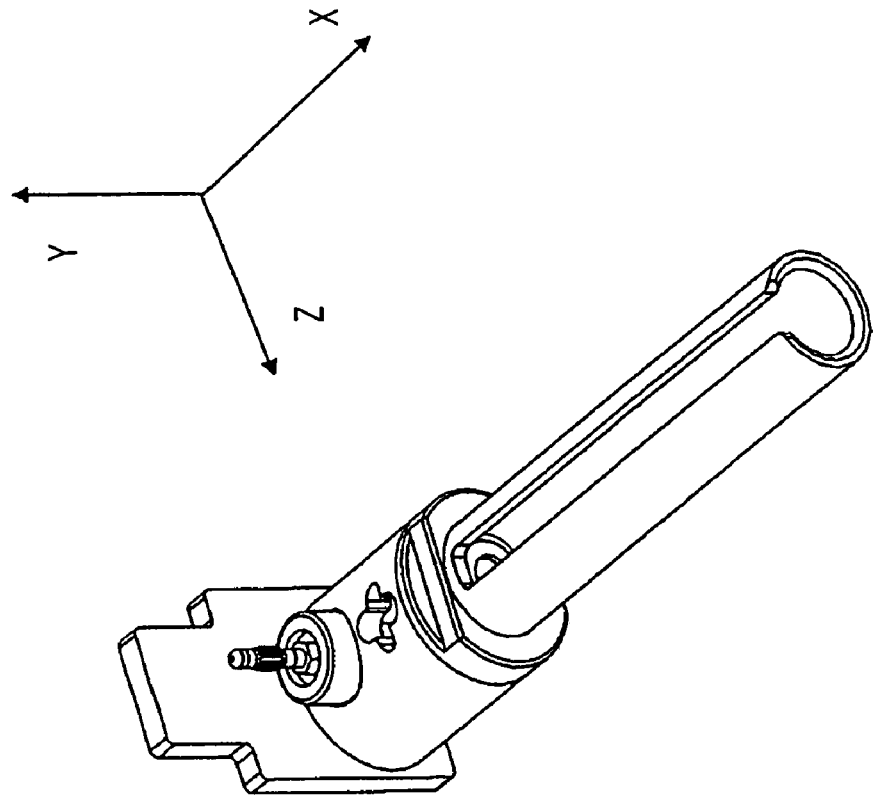
FIG. 4B is a distal perspective view (from above) of the anode buffer chamber and the loading tube of an embodiment of the device of the present invention, with the anode electrode plug operationally engaged in the anode buffer chamber.
Figure 4A:
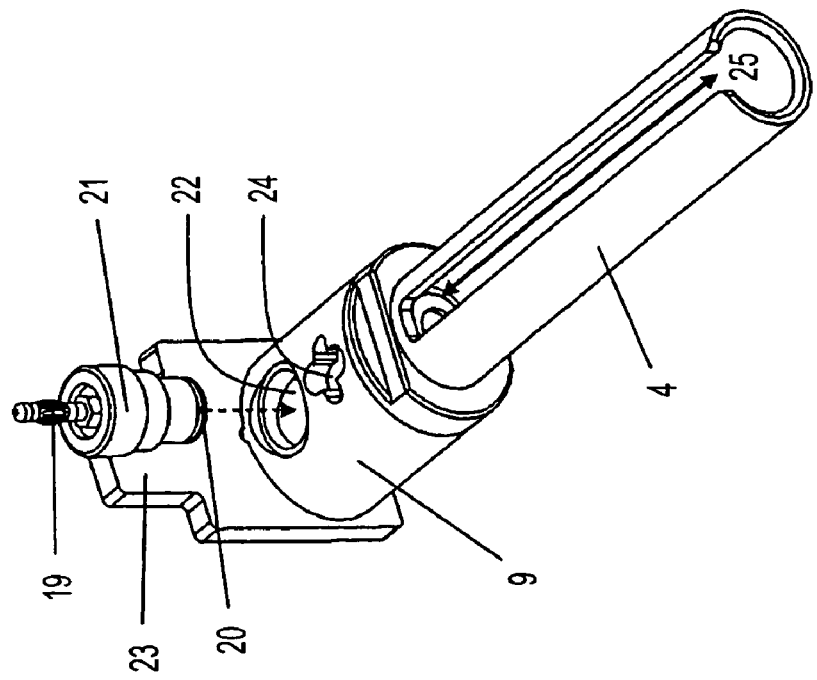
FIG. 4A is a distal perspective view (from above) of the anode buffer chamber and the loading tube of an embodiment of the device of the present invention, with the anode electrode plug disassembled from the anode port.

FIG. 4A shows the loading tube and various components of the anode region of the device shown in FIG. 1 from a distal perspective, viewed from above.

Loading tube 4 holds the components of the chamber stack in coaxial alignment during assembly and operation, as discussed below with reference to FIG. 5A.

Anode plug 21 is the component housing both the anode electrode 19 and the anode wire 20.

Anode electrode 19 is the point of electrical contact of the device with the positive terminal of an external power supply (not shown). Anode electrode 19 is in electrical contact with anode wire 20. In the embodiment shown, anode wire 20 extends from the anode electrode through the interior of anode plug 21.

In other embodiments, anode wire 20 is routed down the outside of anode plug 21. Routing anode wire 20 through the interior of anode plug 21 presents certain advantages, however. For example, if anode plug 21 is made of an insulative material, routing the conductive wire inside the insulative material reduces or eliminates off-axis line charge, which could cause an asymmetrical field.

Anode plug 21 is engaged for use within anode port 22, thus bringing anode wire 20 into contact with the interior of anode buffer chamber 9.

In some embodiments, anode plug 21 is removably engageable with the anode buffer chamber. By removably engageable is meant that the user can remove and replace it in the anode port without damaging the device.

In such embodiments, anode plug 21 is inserted prior to use into anode port 22, as shown in FIG. 4B. In one embodiment, anode plug 21 simply rests in the anode port 22. In another embodiment, anode plug 21 snaps into the anode port 22. In another embodiment, the anode plug 21 screws into the anode port 22.

In certain removable plug embodiments, anode plug 21 is integral with or removably engaged with the lid 1, and is inserted into anode port 22 when lid 1 is engaged with cathode tab 17 and anode tab 23.

In alternative embodiments, anode plug 21 is permanently or semi-permanently sealed within the anode port 22, and may even be integral therewith.

The nature of the connection between the anode plug and the anode port can vary but still be within the scope of the invention.

Anode buffer chamber 9 may also comprise an anode tab 23 configured to fit through the anode tab slot 42 in lid 1 when the device is fully assembled. The size and/or shape of the anode tab 23 may optionally be distinct from the size and/or shape of the cathode tab (discussed above) to ensure that the lid, and thus the electrode cables, may only be attached with the proper polarity. In the embodiment shown in FIGS. 4A and 4B, the anode tab 23 is wide (or long) relative to the cathode tab.

The anode buffer chamber 9 is filled during operation (i.e., during electrophoresis, such as IEF) with an electrically conductive anode buffer, which provides electrical connectivity between the anode wire 20 and the lumen of the chamber stack within the loading tube.

Anode buffer chamber 9 may usefully be designed to have a volume of 10 ml, 15 ml, even 16 ml, 17 ml, 18 ml, 19 ml, or 20 ml or more.

The anode buffer chamber 9 optionally comprises an anode buffer inlet 24 for introduction (or removal) of anode buffer. The anode buffer inlet 24 may optionally have a shape distinguishable from the cathode buffer inlet 18 (shown and discussed above, FIGS. 3A and 3B) to ensure that the user does not introduce the wrong buffer into the anode buffer chamber 9. In the embodiment shown in FIGS. 4A and 4B, the anode buffer inlet 24 is shaped like a "plus sign" (+).

In certain embodiments, anode buffer chamber 9 is transparent, which permits ready visualization of dyes that are capable of migrating to the anode during electrophoresis.

Figure 5A:
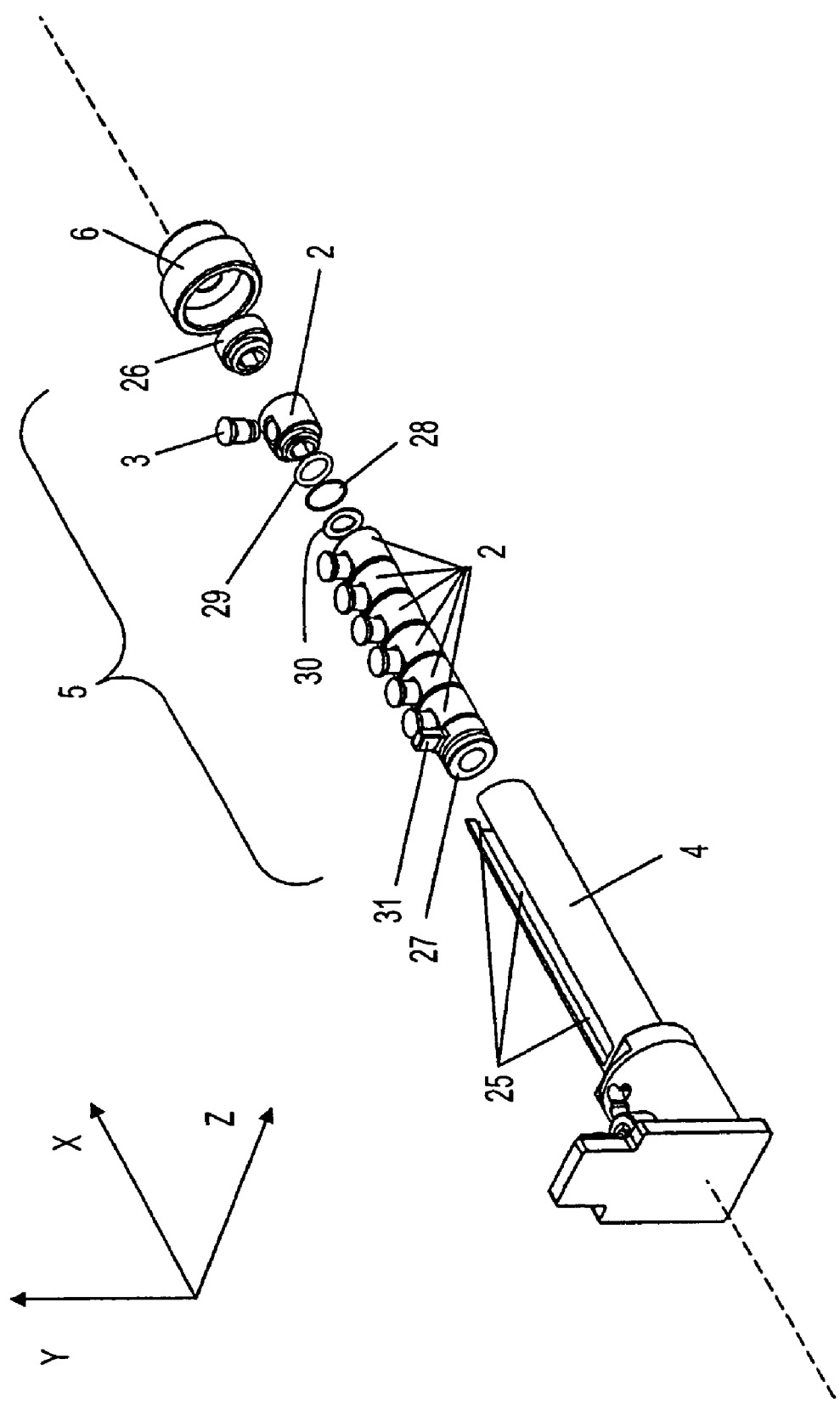
FIG. 5A is a partially exploded proximal perspective view (from above) of the anode buffer chamber, the loading tube, and the chamber stack of an embodiment of the present invention. In this exemplary view, sealing O-ring 29, immobilized buffer disk (IBD) 28, and spacer 30 are all shown positioned between two sample chambers 2; in typical embodiments, however, IBD 28 and spacer 30 are alternatives, and only one of the two is positioned with an O-ring between adjacent sample chambers.
Figure 5B:
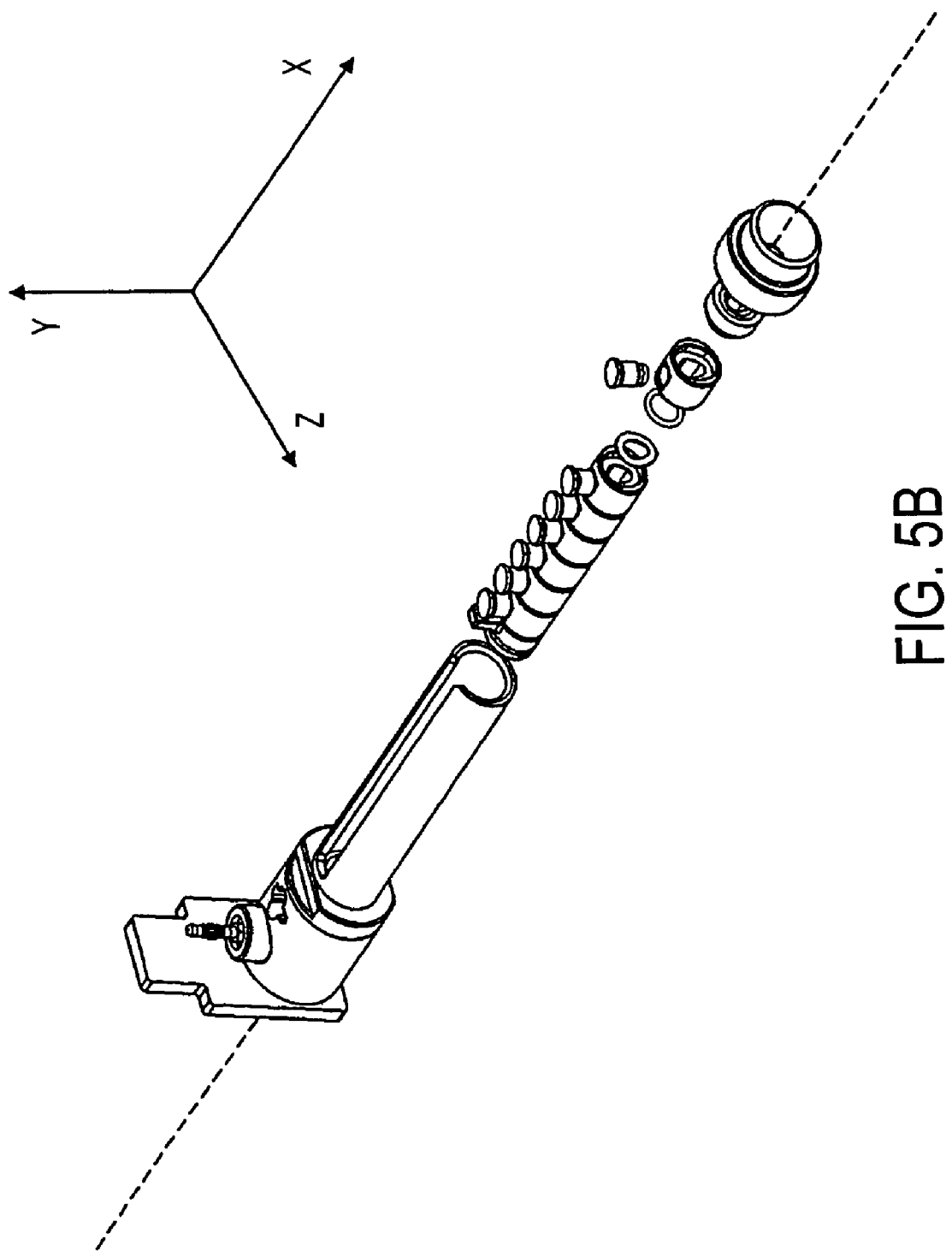
FIG. 5B is a partially exploded distal perspective view (from above) of the same components as in FIG. 5A.

FIG. 5A shows the components of the chamber stack, partially disassembled, from a proximal perspective, viewed from above. FIG. 5B shows the same components from a distal perspective, also viewed from above.

When fully assembled, the chamber stack comprises a plurality of detachable sample chambers aligned along the electrical axis between the anode and cathode; the lumens of the coaxially aligned sample are capable collectively of defining an electrically-conductive fluid column through the chamber stack.

The chamber stack further comprises a plurality of junctional partitions, each of the partitions positioned at a different one of the junctions between the sample chambers. The partitions prevent bulk fluid flow between partitioned chambers, but are both ionically conductive and porous to at least a plurality of the analytes in the sample.

For use in solution phase isoelectric focusing, the partitions have additional features; such partitions are referred to herein as Immobilized Buffer Disks (IBD).

An IBD is a thin membrane disk containing covalently attached buffers of defined pH. For solution phase IEF, IBDs differing in pH are disposed between successive pairs of sample chambers. The IBD most proximal to the anode is the most acidic, and the IBD closest to the cathode is the most basic. The other IBDs are arranged in decreasing order of acidity as they approach the cathodic end of series of sample chambers. In the embodiment shown in the accompanying figures, a total of six different IBDs are used. In one embodiment, the pHs of the six IBDs, from anode to cathode, are 3.0, 4.6, 5.4, 6.2, 7.0, and 10.0.

The first six of the seven sample chambers shown in FIG. 5A, counting from the anode end piece, are shown preassembled. Although only the seventh chamber is shown disassembled, the junctions between all the chambers comprise the components shown explicitly for chamber seven, as discussed below. The various components are discussed first, by way of example, with respect to sample chamber seven, with reference to FIGS. 6A and 6B, and then for all chambers.

Figure 6B:
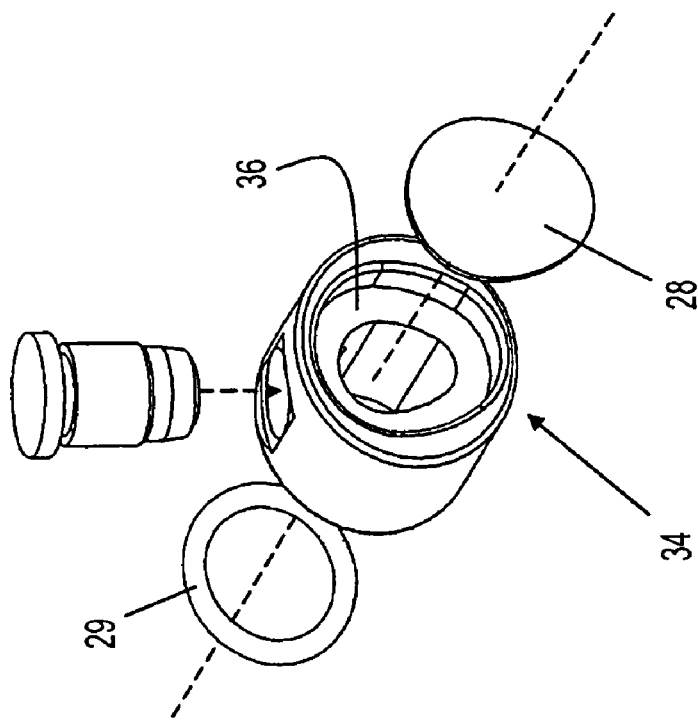
FIG. 6B is an exploded distal perspective view (from above) of one embodiment of a sample chamber according to the present invention, showing the use of an IBD as an alternative to use of a spacer.
Figure 6A:
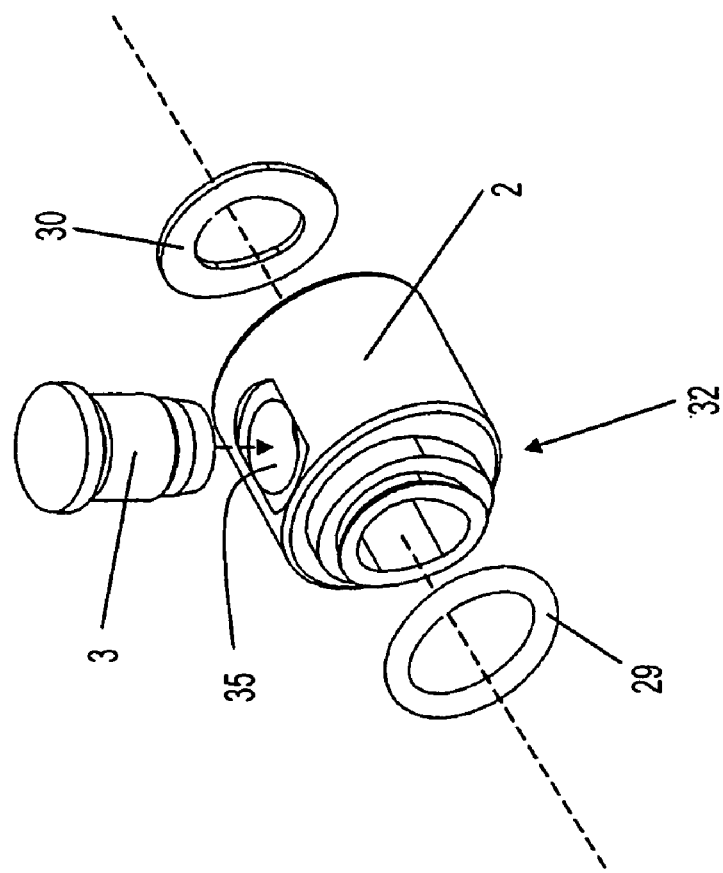
FIG. 6A is an exploded proximal perspective view (from above) of one embodiment of a sample chamber of the present invention, with fill port, a cap seal for the fill port, a sealing O-ring, and a spacer.

Sample chambers 2 have a through bore, or lumen, that extends from the proximal face 32, closest to the anode when in the assembled chamber stack, through the distal face 34, closest to the cathode when in the assembled chamber stack, as illustrated in FIGS. 6A and 6B. FIGS. 1, 2A, 5A, 6A and 6C all show the proximal face of the illustrated sample chambers, whereas FIGS. 5B and 6B show the distal faces of the respectively illustrated sample chambers.

Figure 6C:
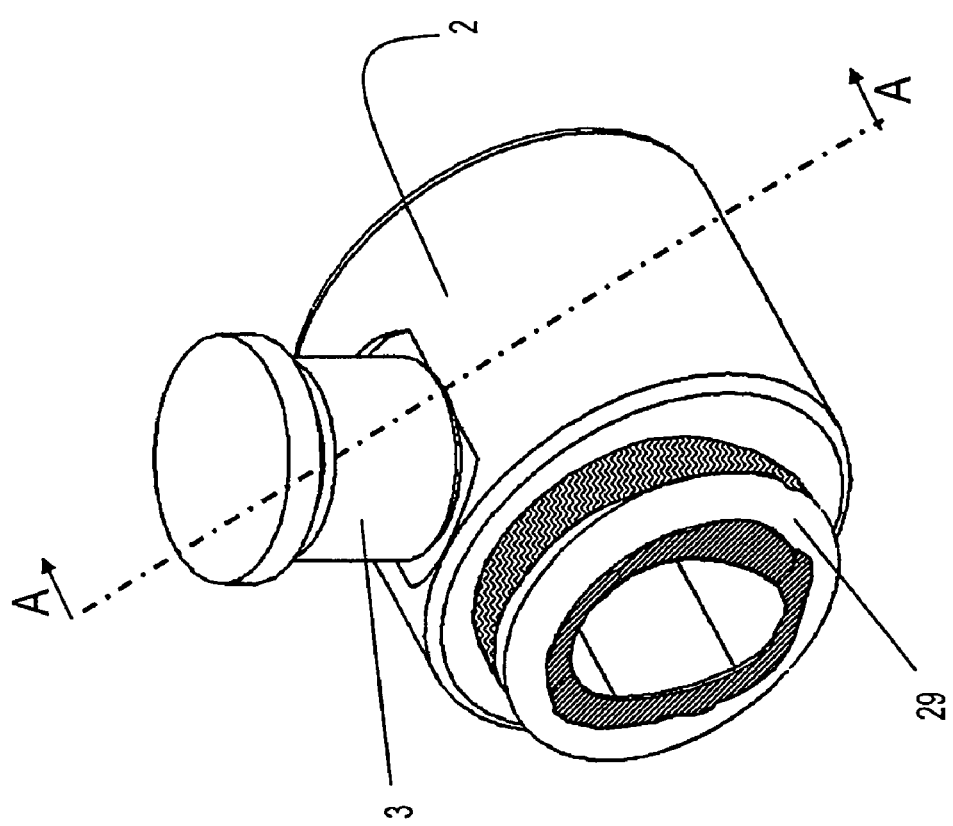
FIG. 6C is a proximal perspective view (from above) of an embodiment of a sample chamber of the present invention showing a cap seal engaged in the chamber fill port, and a sealing O-ring, assembled.

FIG. 6A shows a sealing O-ring 29 positioned near its operational position at proximal face 32 of the sample chamber 2. The proximal face 32 comprises seating means for sealing O-ring 29. In the embodiments shown, the seating means include two concentric projections 33 from a base level. When assembled, the sealing O-ring 29 seats around the second, smaller projection, and against the first of these projections, as illustrated in FIG. 6C.

In typical embodiments, proximal projections 33 typically conform substantially in shape to the shape of the internal lumen of chamber 2. For example, when the lumen is circular, the proximal projections will also typically be circular.

Also shown in FIG. 6A is a spacer 30, shown in exploded view near the distal face 34.

The distal face 34 of chamber 2 is best illustrated in FIG. 6B. In contrast to FIG. 6A, an IBD 28 is shown instead of a spacer 30. In typical embodiments, spacer 30 and IBD 28 are alternatives, and only one of the two is seated in the distal recess 36 in the distal face of sample chambers 2. Spacer 30 will typically have outer dimensions substantially identical to that of IBD 28, and substantially identical thickness. In contrast to IBD 28, however, spacer 30 will have a through bore with shape and dimensions substantially conformal to the shape and dimensions of the chamber lumen. The positioning of a spacer between adjacent chambers thus serves effectively to combine the lumens of the chambers between which it is positioned into a single sample chamber of increased volume.

FIG. 6C shows sealing O-ring 29 assembled on proximal projections 33 of chamber 2.

O-ring 29 acts as a face seal between adjacent chambers: upon assembly, axial compression of the chamber stack compresses O-ring 29 axially onto the surface of either an IBD 28 or spacer 30 seated within distal recess 36 of the next most proximal chamber in the stack. The O-ring holds the IBD or spacer in operational position within distal recess 36, and prevents a free electric path from becoming established around an IBD partition.

The same O-ring contemporaneously creates a gland seal against the walls of the distal recess of the next most proximal chamber in the stack. This aspect of the seal is not activated by axial loading, but instead results from the close fit between the proximal projections 33 and the outer walls of the distal recess 36 which are precisely sized to incorporate the compliant O-ring between them to form the gland seal. This gland-seal function of the single O-ring seal prevents leakage of fluid between the chambers, and conversely prevents external contamination from entering chambers 2. Hence a single seal accomplishes both face seal and gland seal functions.

In other embodiments, an additional O-ring may be positioned within the distal recess of chamber 2, typically external to (i.e., distal to) the IBD or spacer. In yet other embodiments, the O-ring could be positioned first into the distal recess rather than the proximal projection as the two adjacent chambers are assembled.

The structure of the chamber stack as a whole is most easily understood by reference to the process for its assembly. Although illustrated here by a method of assembly, no particular order or method of assembly is required to create a device according to the present invention.

Anode end piece 27 is the first (that is, most proximal) component assembled in the chamber stack (see FIG. 5A). Like chambers 2, anode end piece 27 has a throughbore, or lumen, extending from its proximal face through its distal face. The lumen is typically, in both shape and dimensions, substantially identical to that of the chambers to be assembled thereto.

Also like chambers 2, the anode endpiece may include O-ring seating means on its proximal face. In such case, an O-ring is applied thereto. In other embodiments, however, no O-ring seating means are provided, with seal to anode buffer chamber 9 effected, e.g., with an O-ring integrated into the distal face of anode buffer chamber 9.

Anode endpiece 27 typically comprises a distal recess, analogous to the distal recess on chambers 2.

A spacer 30, an IBD 28, or an alternative partition is typically placed in the anode endpiece distal recess.

In embodiments in which an IBD 28 is used, the first sample chamber may be bounded on both sides by an IBD, and will therefore be able to circumscribe a discrete electrophoretic fraction. When a spacer (with or without a nonconductive semipermeable membrane) is used, the first sample chamber will be unable to circumscribe a discrete electrophoretic fraction.

In other embodiments, an alternative partition may be used. For example, the partition may be an ion-permeable membrane that is nonporous to analytes above a selected molecular weight. If the molecular weight cutoff is small, the partition acts to keep analytes from traveling into the anode buffer chamber.

Next, a first sample chamber, with O-ring assembled on the proximal projections, is added. Alternatively, the O-ring is seated in the distal recess of anode endpiece 27. In this latter embodiment, proximally-directed axial pressure later urges the O-ring onto the proximal projections of the first sample chamber.

The first sample chamber may include an IBD or spacer in its distal recess at the time of its assembly to the anode end piece. Alternatively, the chamber may be assembled to the anode end piece without a spacer or IBD, which is thereafter placed in the distal recess.

A second sample chamber, with O-ring seated on its proximal projections, is then added, and the process is repeated until the desired number of sample chambers has been added.

In an alternative, the O-ring is seated in the distal recess of the first chamber, and the second chamber then assembled thereto; proximally-directed axial pressure then urges the O-ring onto the proximal projections of the next most distal chamber.

The embodiment illustrated in FIGS. 5A and 5B includes seven total sample chambers, although the invention also contemplates the use of fewer or more chambers.

Figure 8:
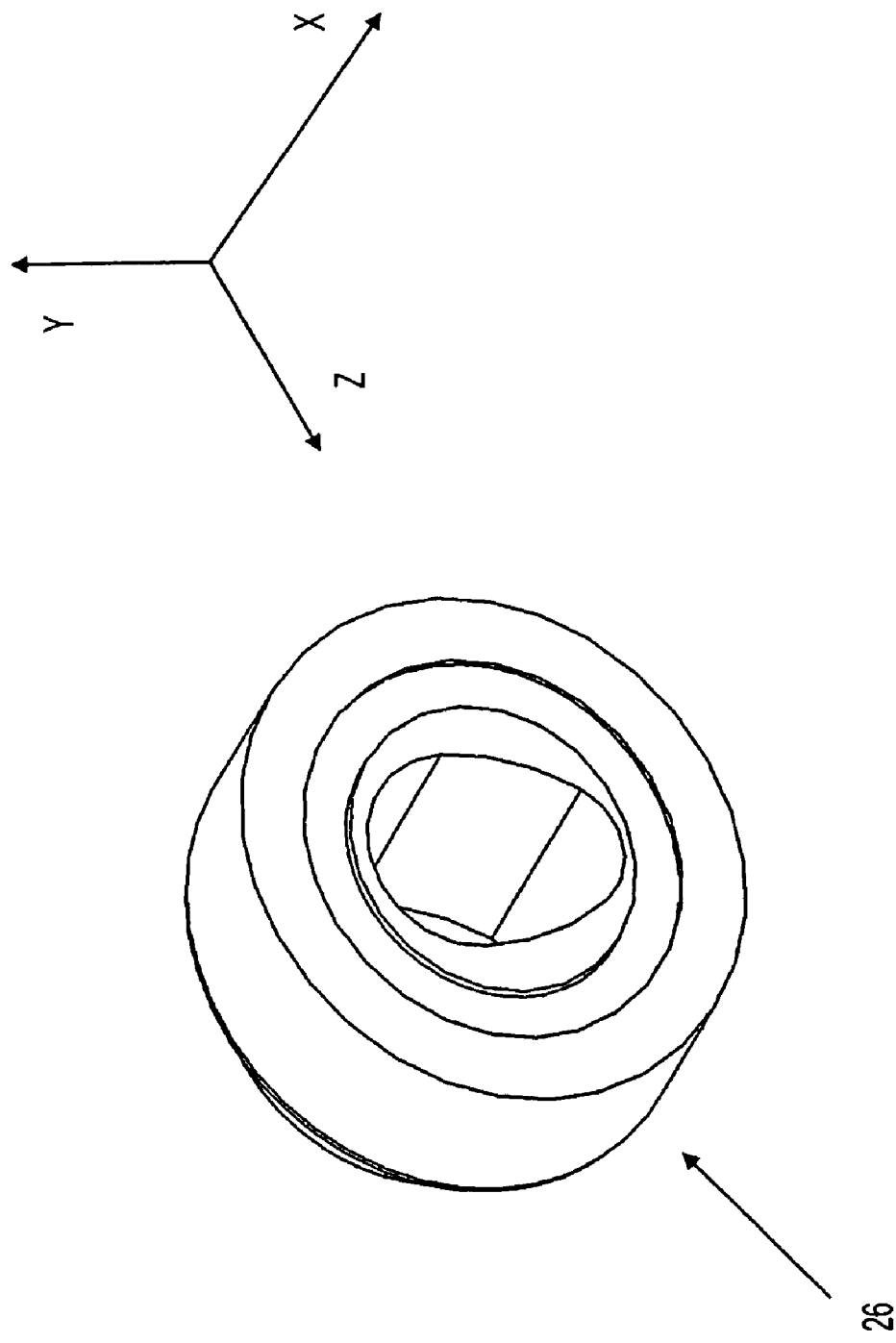
FIG. 8 is a distal perspective view (from above) of an embodiment of a cathode end piece of the present invention; the end piece interfaces the distal-most sample chamber of the chamber stack with the screw cap (not shown).

A cathode end piece 26 (FIG. 5C and in greater detail in FIG. 8) is the last (that is, most distal) component assembled in the chamber stack (see FIG. 5A). Like chambers 2, cathode end piece 26 has a throughbore, or lumen, extending from its proximal face through its distal face. The lumen is typically shaped and dimensioned substantially identically to that of the chambers to be assembled thereto.

Also like chambers 2, the cathode endpiece typically includes O-ring seating means on its proximal face.

Cathode endpiece 26 typically includes a distal recess, into which a spacer, an IBD, or an alternative partition, and additionally or alternatively, an O-ring, are seated.

In the embodiments described above, junctions between sample chambers comprise either an IBD or a spacer. A sample chamber that is not bounded at both proximal and distal faces by an IBD when assembled, but rather by spacers, is referred to as a "blank" chamber.

Zero, one, two, three, four or more blank chambers may be used depending on any given application of choice. For a device with "n" sample chambers, if there are fewer than "n+1" different IBD filters available, blank sample chambers are required to properly fill the loading tube. Alternatively, a user of the device may have access to n+1 IBDs but may chose not to use all of them, in which case blank sample chambers are also used. Users of the device may opt to use fewer than all available IBDs if the amount or number of proteins to be separated is limited, or if he or she is only interested in proteins in a specific range of pI, or for other reasons. The number of sample chambers in the IEF device, the number of blank sample chambers, the number of IBDs and their pHs can vary but still be within the scope of the present invention.

Figures 5C, 5D:
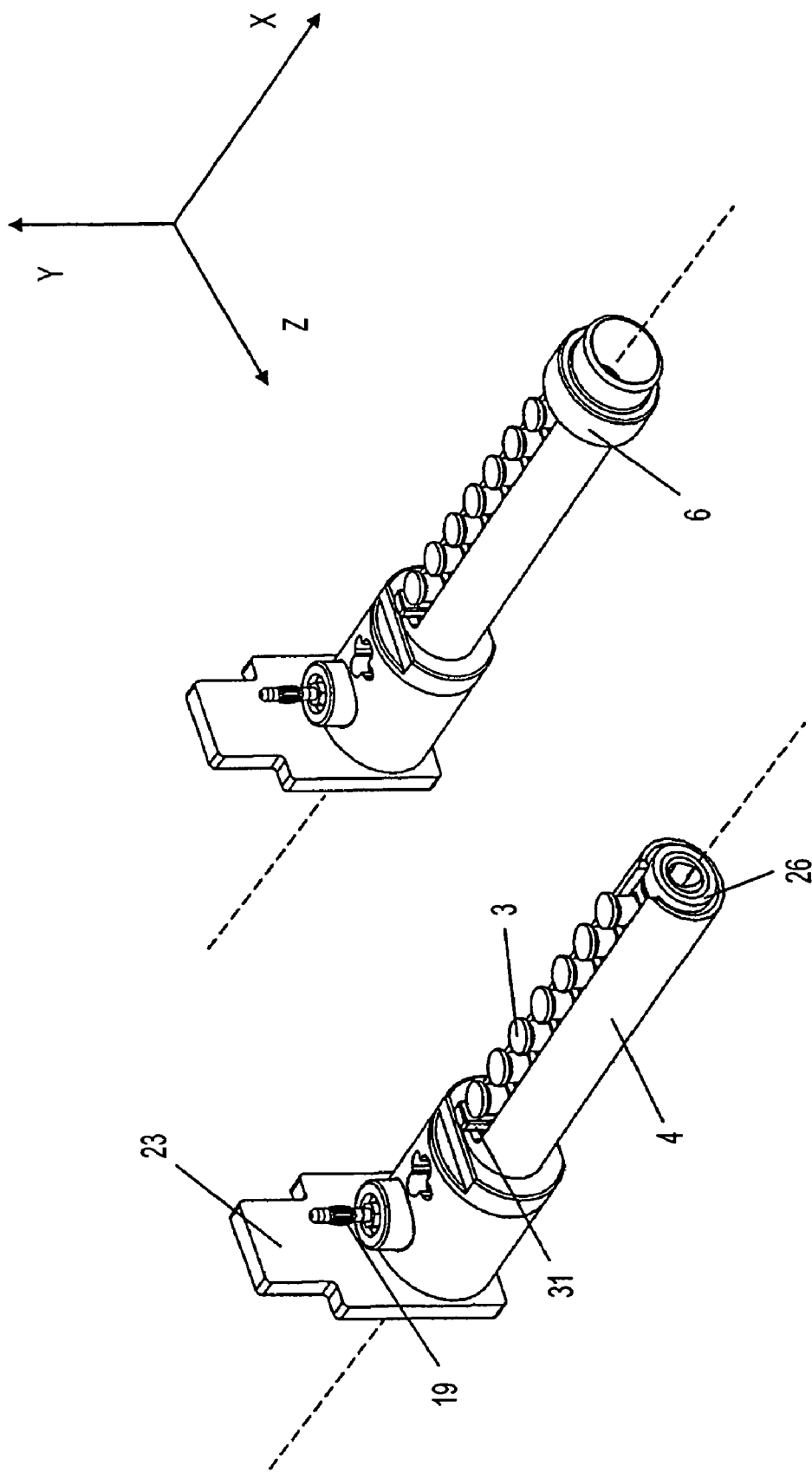
FIG. 5C is a distal perspective view (from above) of the anode buffer chamber, the loading tube, and several sample chambers and associated components of an embodiment of the present invention, assembled, but without the screw cap.
FIG. 5D is a distal perspective view (from above) of the components shown in FIG. 5C, with the screw cap operationally engaged.

The loading tube 4 can be used to facilitate assembly of the chamber stack by holding successive components as they are added, or the chamber stack can be assembled without aid of the loading tube and subsequently inserted into it. FIG. 5C shows the chamber stack loaded in the loading tube.

A removable endcap may be used to constrain the chamber stack within the loading tube.

In useful embodiments, the endcap is capable of applying a proximally directed axial pressure to the chamber stack, urging the chambers and endpieces together, thus facilitating their sealing engagement to one another and to the anode and cathode buffer chambers. In particularly useful embodiments, the endcap is capable of applying a circumferentially uniform, proximally directed, axial pressure. FIG. 5D shows end cap 6 engaged to stacking tube 4, constrained a chamber stack within the tube.

In one series of embodiments, both loading tube 4 and end cap 6 are at least partially threaded, and the thread of the end cap is capable of engaging the thread of the stacking tube (such embodiments of the end cap are called "screw caps" herein). In particularly useful embodiments, the stacking tube thread is external to the stacking tube, and the screw cap thread is internal to the screw cap.

The end cap has a lumen, thus permitting fluid communication between the cathode buffer chamber and the interior of the chamber stack (i.e., with lumens of the cathode end piece and the distal-most sample chamber).

In typical embodiments of the device and components of the present invention, sample chambers 2 include fill ports 35 (see FIGS. 6A and 6B), into which cap seals 3 may be sealingly engaged.

In embodiments in which the fully engaged cap seals 3 are not flush with the outer surface of the sample chambers, loading tube 4 may usefully include an axially oriented channel 25 (see, e.g., FIGS. 4A and 4B) to accommodate the projection of engaged cap seals 3 from the body of sample chambers 2. In such embodiments, cap seals 3 may usefully be inserted into fill ports 35 of sample chambers 2 prior to inserting the chambers into the loading tube 4: the necessary engagement of the projecting cap seals within (or through) the channel during loading ensures that the fill ports of all of the chambers are aligned within the assembled chamber stack.

Usefully, channel 25 of loading tube 4 is positioned at the top side of loading tube 4, aligning the fill ports of chambers 2 of the chamber stack upwards (see, e.g., FIGS. 5C and 5D). This facilitates both fluid addition and removal while the chamber stack is fully assembled.

In addition, chambers 2 may in some embodiments usefully be self-indexing—that is, configured automatically to align their fill ports.

For example, the proximal projections and the distal recesses may usefully lack rotational symmetry. In such embodiments, once the proximal projection of a second chamber is properly mated within the distal recess of a first chamber, the two cannot rotate with respect to one another, ensuring that their fill ports are aligned. Such self-indexing cannot be achieved by chambers that mate by screwing onto one another, since differences in membrane thickness and tightening torque cause the final orientation of any fill port to be arbitrary.

In certain embodiments, the chamber lumen may advantageously conform substantially to such rotationally nonsymmetric shape.

Conforming the shape of the lumen to the shape of the proximal projections and distal recess minimizes the area of the IBD outside the "active" field area, which minimizes the amount of analyte that migrates into the IBD outside the "active" field area and is lost to the fractionation process.

Conforming the shape of the lumen to the shape of the proximal projections also makes diffusive losses from the active to inactive areas of the IBD uniform around the IBD circumference, by making uniform the distribution of inactive IBD areas.

Hence, in certain useful embodiments, the chamber lumen itself follows the shape of the seal, offset inwardly and uniformly from the internal edge of the distal recess.

The lumen of the sample chamber may also advantageously be nonsymmetric across the horizontal plane (i.e., when the device is horizontal in use).

In some embodiments, for example, the chamber lumen may usefully have a more acute radius of curvature at the bottom than at the top: as liquid sample is removed after fractionation, this geometry facilitates the pooling of the remaining fluid at the bottom of the chamber, thus facilitating the complete withdrawal of the sample after electrophoresis. In other embodiments, the more acute radius of curvature is at the top: this facilitates expression of air from the chamber as the chamber is capped before electrophoresis.

Figure 7B:
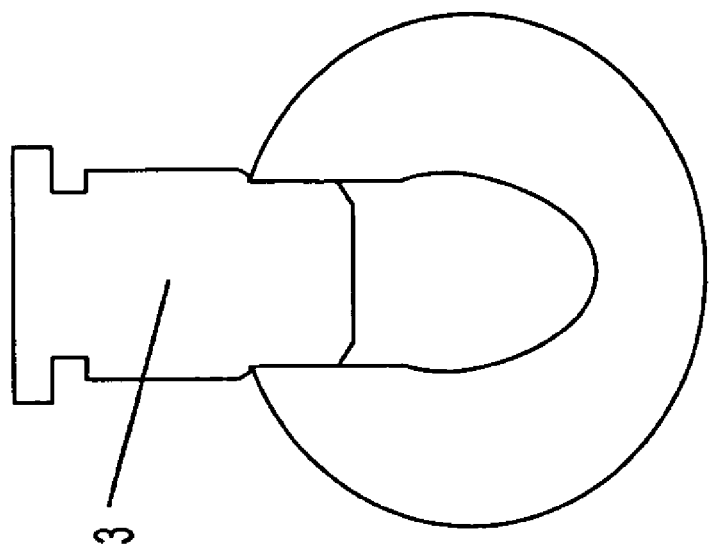
FIG. 7B is an orthogonal midsectional view of the sample chamber of FIG. 7A, showing a cap seal operationally inserted into the fill port.
Figure 7A:
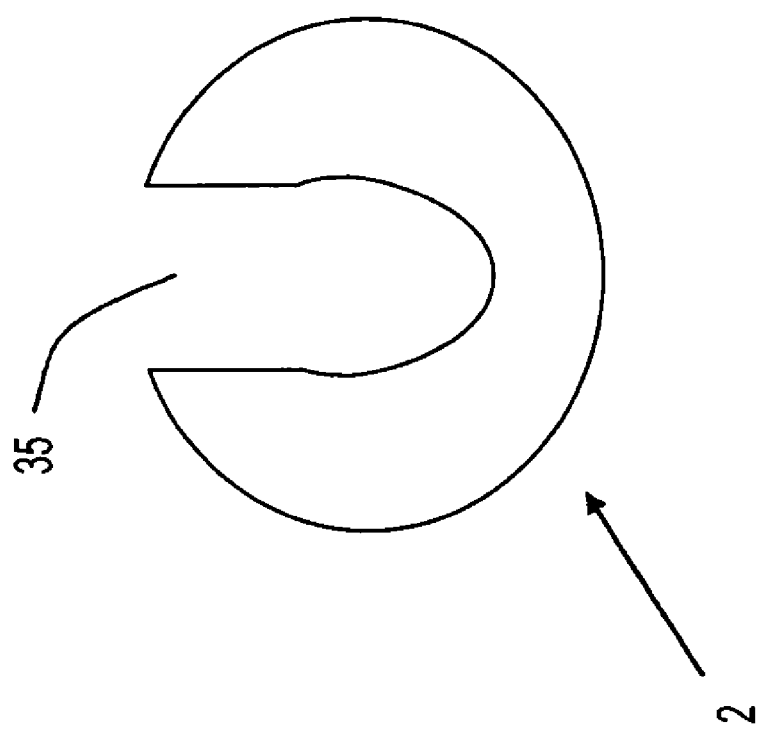
FIG. 7A is an orthogonal midsectional view of an embodiment of a sample chamber of the present invention, viewed along line A-A of FIG. 6C, showing the fill port.

FIGS. 7A and 7B present orthogonal midsectional views of an embodiment of a sample chamber of the present invention, viewed along line A-A of FIG. 6C. FIG. 7B illustrates the operational engagement of cap seal 3 within fill port 35. In the embodiment shown, the chamber lumen is a rotationally nonsymmetric ovoid (pseudoellipse) (further described below).

Figure 7E:
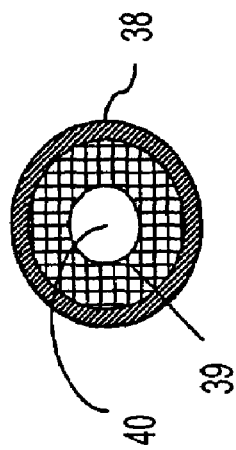
FIG. 7E is a bottom orthogonal view of an embodiment of the cap seal of FIG. 7D.
Figure 7D:
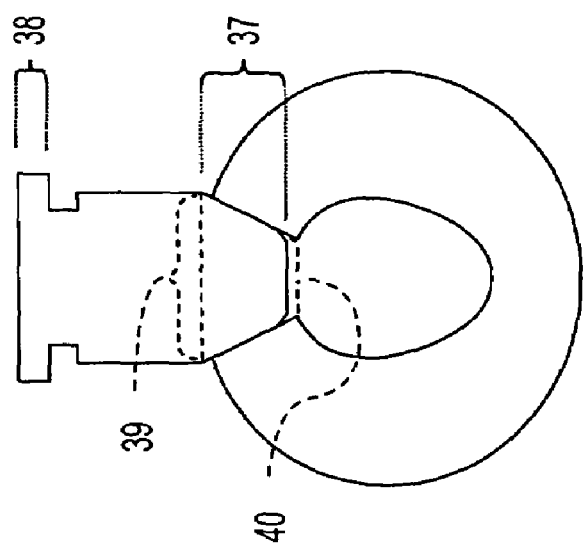
FIG. 7D is an orthogonal midsectional view of the sample chamber of FIG. 7C, showing an alternative cap seal, properly dimensioned to seal the tapered fill port, engaged within the fill port.
Figure 7C:
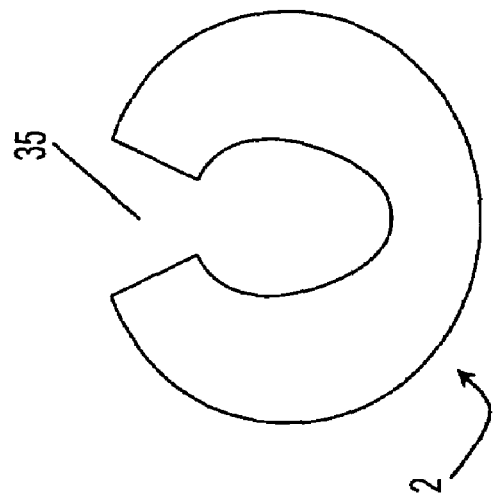
FIG. 7C is an orthogonal midsectional view of an alternative embodiment of a sample chamber of the present invention having a tapered fill port, viewed along line A-A of FIG. 6C.

FIGS. 7C and 7D present orthogonal midsectional views of another embodiment, in which the fill port 35, and the corresponding portion of the cap seal 3, is tapered. The cap seal fits in the fill port tightly enough to prevent sample evaporation but is readily removable by hand. FIG. 7E shows an orthogonal view of the cap seal of FIG. 7D, from the bottom. The concentric circles define the cross-sectional areas at three planes within the cap seal, as described in more detail below.

FIG. 9A illustrates the lid 1 for the device shown in FIG. 1. Lid 1 protects the user from electrical shock and, when spill tray 7 includes distinguishable anode and cathode tabs, helps to ensure proper electrical connection polarity.

Lid 1 optionally comprises an anode cable 41 and a cathode cable 43 that connect the anode electrode 19 and the cathode electrode 13 to their respective outlets on an external power supply (not shown) when the lid is operationally seated on the device, as shown in FIG. 9B. The electrode cables can be permanently attached to lid 1 or removable therefrom.

In one embodiment, the electrode cables 41 and 43 are permanently or semi-permanently attached to the lid such that they are not intended to be removed by the user. In such embodiments, the electrode cables are optionally color coded to facilitate connection with proper polarity. In some of these embodiments, the electrodes are positioned in the lid so that they become submerged in the anode and cathode buffer chambers when the lid is placed onto the apparatus, without the intermediation, respectively, of anode and cathode plugs.

In other embodiments, the electrode cables 41 and 43 are detachable from the lid 1. In such embodiments, holes in the lid above the anode and cathode electrodes allow the electrodes to protrude, or cables to enter the device, to effect electrical connection. In another embodiment (not shown), prominent markings on the lid, e.g. color coded markings or "plus" and "minus" signs, may be placed on the lid at or near the anode and cathode holes to clearly indicate to the user which power cord to attach to which electrode.

In certain embodiments, lid 1 also comprises an anode tab slot 42 and a cathode tab slot 44, which optionally differ in size and/or shape. This size and/or shape difference makes it possible to attach the lid in only one orientation with respect to the electrodes, i.e. with a defined electrical polarity.

The lid also enhances safety by preventing human contact with the electrode or buffers during operation, since the interior of the device can only be accessed with the lid removed, which necessarily disconnects the device from the external power supply.

Lid 1 may optionally, but advantageously, be transparent, to permit visualization of the loading tube, chamber stack, and other components during electrophoresis.

To perform solution phase IEF using a device of the present invention, the chamber stack is first assembled using a plurality of IBDs, each having a different, fixed, pH. A protein sample of interest is introduced into one or more sample chambers through their respective fill ports, and sealed without trapped air using, for example, a tapered cap seal and a tapered fill port. Any sample chambers not filled with protein are filled with sample diluent, which will typically have a low salt concentration. Appropriate anode and cathode buffers are introduced through the respective anode and cathode buffer chamber inlets, and electrode plugs are screwed into the electrode ports. The lid is then put on the device, and the electrodes connected to the appropriate terminals on an external power supply.

An electric potential is applied to the device until each protein reaches the chamber bounded by IBDs that bracket its pI.

The electrical potential is generally at least about 50 V, 100 V, 150 V, or 200V to about 1000 V, 1500 V, even as high as 2,000 V-3,000, with values between 50 V and 3000 V useable. The potential may be changed within this range during electrophoresis.

Power is turned off, the lid is taken off and samples are removed from the sample chambers and stored as IEF fractions defined by the IBDs bounding each Chamber.

The device and methods of the present invention do not require sample mixing or recirculation during fractionation, or means therefor. In other embodiments, however, the entire device, such as that shown in FIG. 9B, is placed on a rocking or rotary platform during electrophoresis. The gentle, externally applied, motion of the sample chambers mixes samples in order, for example, to prevent precipitation of proteins at the surface of the IBD membranes and/or electrodecantation.

External agitation of the device of the present invention is preferable, for example, to recirculation of sample through long tubing and through peristaltic pumps, as in several prior devices. Such recirculation exposes samples to greatly increased surface area, with consequent losses of surface-adherent components, e.g. proteins. Recirculation also requires that the volume of sample be increased substantially beyond the volume of the sample chamber. Surface losses and dilution are particularly disadvantageous with small amounts of protein.

External agitation is also superior to internal agitation using stir bars in each sample chamber. Unlike stir bar devices, the device of the current invention, coupled with external agitation, does not require introduction of a foreign part into each sample, and does not involve a series of fragile moving parts.

The device of the present invention enables solution phase IEF fractionation of relatively small volumes of sample, e.g. about 0.6 ml, 0.7 ml, 0.8 ml, 0.9 ml, even 1.0, 1.5, 2.0, and 3.0 ml, with intermediate values permissible, such as 0.61, 0.62, 0.63, 0.64, 0.65, 0.66, 0.67, 0.68, and 0.69 as exemplary volumes. Relatively small scale protein preparations can be used in such devices, making it possible to perform solution IEF as a prefractionation step on a number of samples prior to analysis on 2D gels.

The device of the present invention can concentrate protein samples as well as fractionate them.

In contrast, many of the prior devices capable of solution phase IEF are most suited to solution IEF of preparative scale protein samples, rather than analytical scale samples.

Further Advantages of Component Embodiments

Electrode Plugs

Cathode plug 15, illustrated in FIGS. 3A and 3B, and anode plug 21, illustrated in FIGS. 4A and 4B, are collectively referred to herein as electrode plugs.

As described above, the electrode plugs can usefully be removable from their respective ports for ease of cleaning, repair or replacement. In particularly useful embodiments, the electrode plugs are identical to or otherwise interchangeable with one another: this permits the plugs to be used at either end, and permits a single spare electrode plug to serve as a replacement for either a cathode plug or an anode plug that is lost or damaged.

Typically, the electrode plugs according to the present invention are substantially cylindrical.

Figure 14B:
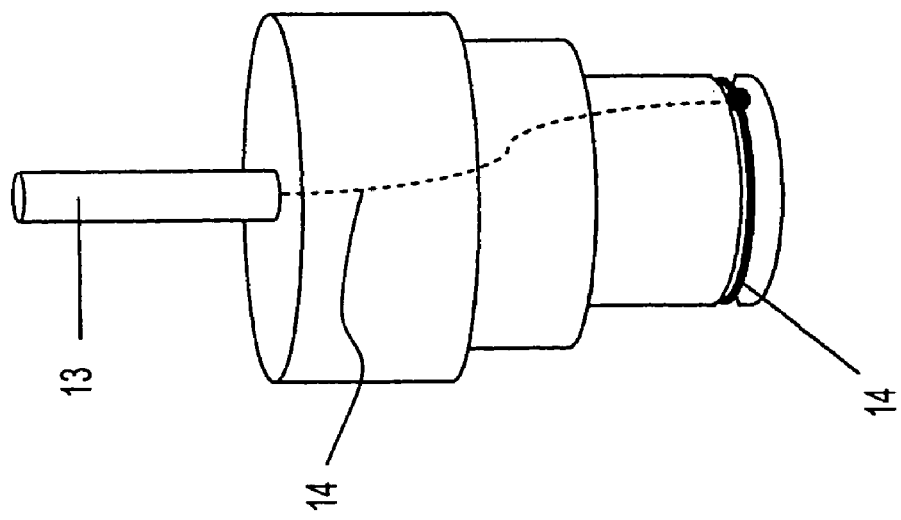
FIGS. 14A and 14B show an exemplary embodiment of a cathode plug of the present invention.
Figure 14A:
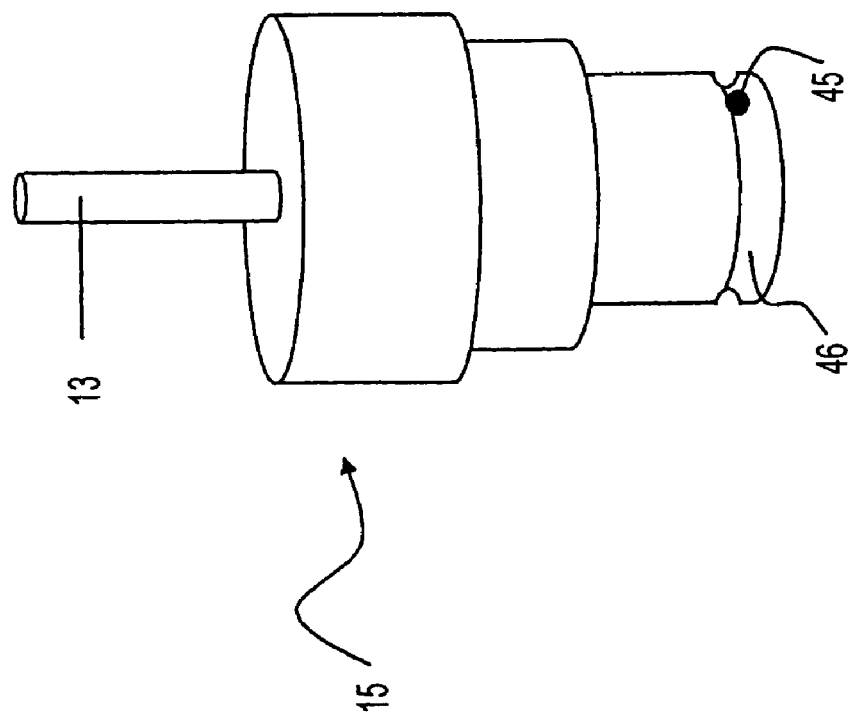

FIGS. 14A-14B show an exemplary embodiment of a cathode plug (equivalently, anode plug) in which the electrode wire advantageously passes through the inside of an insulative plug.

FIG. 14A is a perspective schematic view from above of such an embodiment, without the electrode wire, particularly indicating the outlet 45 for traversal of the wire from the plug interior to its exterior, and an optional circumferential detent 46 near the plug bottom, around which the electrode wire wraps. FIG. 14B shows the plug of FIG. 14A with the electrode wire passing from electrode, through the insulative plug interior, out through the outlet, and around the circumferential detent.

Circumferential positioning of the electrode wire renders the circle of cathode wire co-planar with the circle of anode wire during use. This, in turn, ensures that the shortest distance between the anode and cathode remains the same regardless of the final rotational position of either plug within its respective port. This eliminates variation in the field strength imposed by inconsistencies during assembly or re-assembly.

Recessing the wire within a circumferential detent on the electrode plug protects the electrode wires from being bent or broken during handling, particularly cleaning. Such damage is a common problem with prior devices in which electrode wires are not fully protected. Consequently, electrode wires in the electrode plugs of the present invention need not be as thick as electrode wires in other devices, with consequent cost savings. These advantages apply particularly to electrode wires comprising platinum.

Loading Tube

The loading tube holds the anode end piece, sample chambers, IBDs and optionally spacers, and cathode end piece in the proper coaxial alignment, both during assembly and in operation. As described in detail above, the entire chamber stack can be assembled by stepwise addition of new components, using the loading tube to support those components already assembled. Once assembled, the components are necessarily axially aligned along the electric field gradient.

In certain embodiments, loading tube 4 is transparent, permitting readily visualization of the chamber stack within the tube, facilitating correct assembly of the chamber stack and monitoring for problems within the stack, such as leakage, during electrophoresis.

Certain embodiments of the loading tube include axial channel 25, usefully positioned through the top surface of the loading tube. The channel accommodates cap seals that do not make a flush engagement with the sample chambers, and positioned at the top surface of the loading tube, usefully aligns the chamber fill ports upwardly.

Upward positioning of the fill ports allows loading and unloading of the liquid solutions with a minimum of spillage. In addition, upward positioning of the fill ports allows gas bubbles to float into and be captured a region that is capable of serving as a bubble trap (see below). As would be readily understood, if the fill port were too far from vertical, i.e., on the side or at the bottom of the sample chamber then liquid would spill out when it was opened, and gases formed during the electrophoresis would rise up to the top of the sample chamber and be trapped there rather than in the bubble trap.

In certain embodiments, the anode end piece, which may lack a fill port, includes a protrusion The protrusion of the anode end piece, like the projections of the sample chamber cap seals, is accommodated by channel 25 of loading tube 4. The anode end piece protrusion is useful in disengaging all components of the chamber stack out of the loading tube during disassembly of the device.

End Cap

End cap 6 provides a proximally directed axial force that ensures a tight seal between components of the chamber stack during assembly and use. In some embodiments, as described above, end cap 6 is a screw cap.

Use of an end cap readily permits a circumferentially uniform axial pressure to be applied to the chamber stack; such circumferentially uniform pressures are difficult to achieve with prior devices that require four separate nuts to be tightened onto independent alignment rails.

In embodiments in which end cap 6 is a screw cap, engagement of the sample chamber cap seals within the loading tube channel prevents the sample chambers from rotating relative to one another and/or to the loading tube as the screw cap is tightened. Rotation of chambers and/or end pieces of the chamber stack may also be constrained by use of self-indexing, rotationally nonsymmetric proximal projections and distal recesses.

Tapered Cap Seal and Fill Port

Figure 10B:
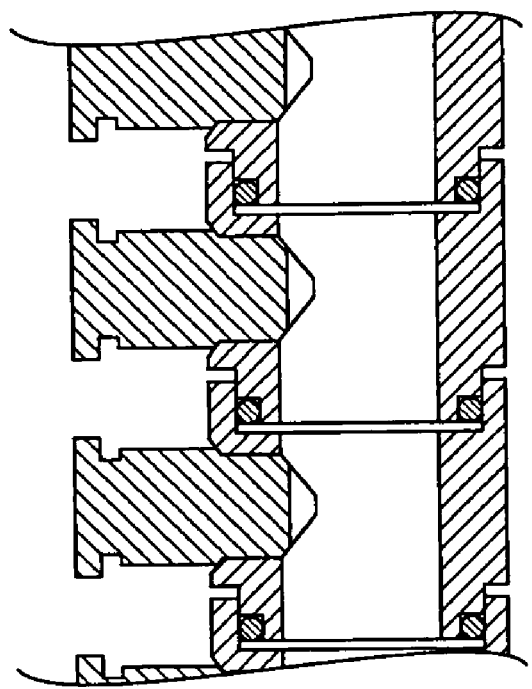
FIG. 10B shows the cap seals engaged within the sample chambers of FIG. 10A.
Figure 10A:
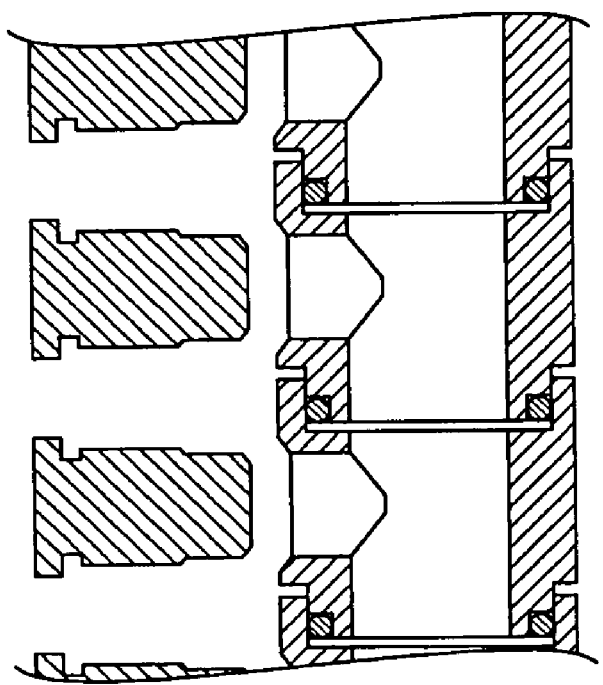
FIG. 10A is a partial side midsectional view of several sample chambers assembled into a chamber stack, according to one embodiment of the present invention, exploded to show the cap seals positioned for insertion.

FIG. 10A is a partial side midsectional view of several sample chambers assembled into a chamber stack, according to one embodiment of the present invention, exploded to show the cap seals positioned for insertion. FIG. 10B shows the cap seals engaged within the sample chambers of FIG. 10A.

The fill ports provide a variety of advantages.

First, the aligned fill ports in the assembled chamber stack allows for the loading of sample and/or buffers into the sample chambers after the apparatus is fully assembled, rather than serially during a manual assembly process, as is the case with other devices.

Second, the ports allow the fractionated samples to be extracted, e.g. with a pipette, directly from each chamber immediately after electrophoresis rather than, as is the case with other devices, from individual chambers as the device is dissembled. This reduces the risks of contamination and loss of sample due to spillage. Moreover, the contents of each chamber can be removed in any order rather than in the order of disassembly. For example, it may be desirable to extract the electrophoresis sample from a particular chamber as quickly as possibly rather than having to wait for other chambers to be removed first.

Third, the filling port creates a "bubble trap" that allows gas bubbles that form during electrophoresis to rise and collect in a region that is outside of the electric field. This is desirable because electric current only conducts through the solution and not through the air/gas bubbles, and the analytes are present only in solution. Not only can air bubbles thus distort the electric field, they have been known to form in other electrophoretic systems and expand to the point where the gas actually occludes the fluid path to such a degree that it blocks the conduction path and therefore the entire electrophoretic process. By allowing bubbles to collect outside of the electric field, the fill ports help to maintain the field constant in cross-section and therefore uniform in density and electromotive force (EMF) across the entire IBD surface throughout the electrophoretic run.

In some embodiments, as illustrated in

FIGS. 7C and 7D, the walls defining fill port 35 are usefully designed so that air or other gas or supernatant fluid is expressed, rather than trapped, as cap seal 3 is inserted into fill port 35 to seal the sample chamber. In the embodiments shown in FIGS. 7C and 7D, the tapered cap seal does not fully block the fill port until the cap seal is fully inserted, giving any air in the fill port the opportunity to escape prior to closure.

In such embodiments, the volume of trapped air that is compressed upon final engagement of the cap seal within the fill port is reduced, reducing the pressure within the sample chamber and keeping the pressure below that which destructively displaces the gel from the IBD, or causes a fluidic leak.

This feature also limits or prevents contamination of the fluid due to airborne substances in the sample chamber.

Alternatively, or in addition, the tapered cap seal may be used to displace a supernatant fluid (other than air) overlaying the sample in the sample chamber and fill port. For example, in circumstances where the sample volume is less than that required to completely fill the sample chamber, it may be desirable to add a supernatant fluid to displace any air that would otherwise remain in the sample chamber. Such fluid may be added to fill not only the sample chamber but also a portion of the fill port, to ensure that absolutely no air remains. When the tapered cap seal is inserted into the fill port it will displace any excess supernatant fluid from the fill port (causing it to overflow out from the top) before finally sealing the sample chamber. The combination of a supernatant fluid to displace air, and the tapered cap seal to allow escape of excess supernatant fluid, facilitates sealing of sample chambers without unwanted air bubbles.

Any one of a number of supernatant fluids may be used to displace air from sample chambers. The only requirements for the fluid are that it not be miscible with the sample (which will typically be in aqueous solution), that it be less dense than the sample, and that its components not interact in undesirable ways with the sample. For example, mineral oil or 1-butanol may usefully be employed as an air displacing supernatant fluid.

With reference to FIG. 7D, the dimensions of the tapered region 37 of a tapered cap seal may be expressed as the ratio of the cross sectional area of the cap seal at the top 39 of the conical region divided by the cross sectional area at the bottom 40 of the conical section. FIG. 7E presents an orthogonal view from the bottom of the tapered cap seal. The smallest, inner circle in FIG. 7E represents the cross sectional area at the bottom of the conical section, and the mid-sized circle represents the cross sectional area at the top of the conical section. The outermost circle is the cross sectional area of the knob.

The taper can be expressed as the ratio of the areas of the mid-sized and inner circles, or by the percentage by which the cross sectional area of the mid-size circle exceeds the cross sectional area of the inner circle. In the embodiment represented in FIG. 7E, the area of the mid-sized circle is approximately 4.4 times the area of the inner circle. For this embodiment, the cross sectional area at the top of the conical region of the cap seal exceeds the cross sectional area at the bottom of the conical region by 340%. In other embodiments of the present invention (not shown), the cross sectional area at the top of the conical region of the cap seal exceeds the cross sectional area at the bottom of the conical region only slightly, or by 20%, 50%, 100%, 200%, 400% or more. The precise value of the taper may vary but still be within the scope of the present invention.

Immobilized Buffer Disks (IBDS)

In another aspect, the invention provides immobilized buffer disks (IBDs; synonymously, "disks"); in certain embodiments, the IBDs are particularly adapted for use in the devices of the present invention.

As used herein, the term "disk" does not intend that the IBD necessarily present a circular surface as viewed along the electrical axis of the device; the shape of the IBD will typically conform to the shape of the sample chamber lumen, which as further described herein may advantageously lack rotational symmetry.

The IBDs of the present invention, when positioned as partitions between adjacent sample chambers in a chamber stack, are capable of interrupting bulk fluid flow through the chamber stack, but are nonetheless permeable to ions and at least a plurality of analytes desired to be analyzed. For use in solution phase isoelectric focusing, the disks have a fixed pH.

The IBDs comprise a porous support and a gel. In typical embodiments, the gel at least partially fills voids within the support.

In general, the support material should provide voids for gel inclusion and lack facial charges. The support can be constructed, for example, from glass fiber microfilter materials, such as Whatman GF/A, GF/B, GF/C, and GF/D filter material (Whatman Inc., Clifton, N.J., USA). In other embodiments, the support can be constructed of polyethylene, such as flash-spun polyethylene (Tyvek®, E.I. DuPont de Nemours, Del., USA), fritted polyethylene (Porex Corp., Fairburn, Ga., USA), sintered polyethylene, or bonded spun polyester fibers. In yet other embodiments, the support can include cellulose filters, cotton nonwoven fabrics, and nylon tulle fabric.

The supports of the present invention are typically thin, ranging in thickness from about 0.1 mm, 0.2, 0.3, 0.4, 0.5, 0.6, 0.7, 0.8, 0.9, 1.0, 1.1, 1.2, 1.3, 1.4 to about 1.5 mm, preferably from about 0.4 to about 1.0 mm, most preferably from about 0.6 to about 0.8 mm. In one embodiment, the supports of the present invention have a width of about 0.65 mm, typically from about 0.64-0.68 mm.

Typically, the completed IBD is at most insubstantially thicker than the support, and the IBD thus typically ranges in thickness from about 0.1 mm, 0.2, 0.3, 0.4, 0.5, 0.6, 0.7, 0.8, 0.9, 1.0, 1.1, 1.2, 1.3, 1.4 to about 1.5 mm, preferably from about 0.4 to about 1.0 mm, most preferably from about 0.6 to about 0.8 mm. In one embodiment, the IBDs of the present invention have a width of about 0.65 mm, typically from about 0.64-0.68 mm.

The support is impregnated (i.e., its void volume substantially filled) with the gel material (acrylamide, agarose, etc.) of choice.

In embodiments in which the gel is a polyacrylamide gel, some formulations previously used in the art result in gel that tends to "ooze out" of the disks. In order to prepare disks having a minimal thickness that can nonetheless meet the structural requirements, the exemplary formulations set forth in Table 1, below, may be used.

TABLE 1

EXEMPLARY IBD FORMULATIONS

| Formula | % Acrylamide (w/v) | Crosslinker as w/w % of acrylamide | Ratio of acrylamide to crosslinker w/w |
|---------|--------------------|------------------------------------|----------------------------------------|
| I | 5 | 4 | 25 |
| II | 10 | 4 | 25 |
| III | 5 | 8 | 12.5 |
| IV | 5 | 10 | 10 |
| V | 6 | 8 | 12.5 |
| VI | 6 | 10 | 17 |
| VII | 7 | 3 | 33 |
| VIII | 7 | 4 | 25 |
| IX | 7 | 5 | 20 |
| X | 7 | 6 | 17 |
| XI | 7 | 8 | 12.5 |
| XII | 7 | 9 | 11 |
| XIII | 7 | 10 | 10 |

In an IBD of the present invention, the w/v percentage of the total acrylamide concentration in the final gel (% T) can be as low as 4%, although % T is typically higher, such as 5%, 6%, 7%, and may be as great as 8%, 9%, even 10%, or more, with nonintegral values permissible within the acceptable range. The percent w/w of crosslinker to total acrylamide (%

C) may be as low as 4%, and may be as high as 5%, 6%, 7%, 8%, 9%, 10%, 11%, 12%, 13%, 14% even as high as 15%, with nonintegral values permissible within this range.

When used for solution phase isoelectric focusing, the IBDs will have a fixed pH, and the gel of the IBD will typically further comprise at least one species of copolymerized pH-conferring monomer.

In one series of embodiments, the copolymerized pH-conferring monomer is an acrylamido buffer monomer. As is known in the art, acrylamido buffers are non-amphoteric weak acids and bases having a vinyl moiety for incorporation into the gel matrix.

Acrylamido buffer monomers useful in the IBDs of the present invention are known in the art. A number of commercially available acrylamido buffers (Amersham Biosciences, Piscataway, N.J., USA, and Sigma-Aldrich, St. Louis, Mo., USA) include: 2-acrylamido-2-methylpropane sulfonic acid; 2-acrylamidoglycolic acid; N-acryloylglycine; 4-acrylamidobutyric acid; 2-morpholinoethylacrylamide; 3-morpholinopropylacrylamide; N,N-dimethylaminoethylacrylamide; N,N-dimethylaminoethylpropylacrylamide; and N,N-diethylaminopropylacrylamide.

In some embodiments, the gel will include a copolymer of acrylamide, N,N'-methylene-bis-acrylamide, and at least one species of acrylamido buffer monomer.

In other embodiments, the copolymerized pH-conferring monomer is a dicarboxylic acid.

The dicarboxylic acid may usefully have the formula:

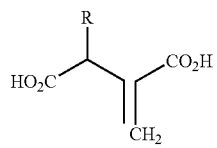

in which R is selected from the group consisting of: —H, —OH, —CH$_2$OH, —CO$_2$H, —NHR', —OCH$_3$, and —NR'R", —Cl, —F, —I, and wherein R' and R" are each independently selected from the group consisting of —CH$_3$, —CH$_2$CH$_3$, —CH$_2$OH, —CH$_2$CH$_2$OH, —CH$_2$CH$_2$CH$_3$.

Use of dicarboxylic acids as copolymerized pH-conferring monomers presents significant advantages. The advantages are particularly evident for IBDs having pH fixed in the range of about 5.0 to about 6.0 with itaconic acid as the pH-conferring monomer.

Previously, disks and strips (such as IPG strips) in the pH range of about 5.0 to 6.0 have required high percentages of acrylamido buffers, for example as much as 10% v/v of gel, in order to achieve adequate buffering strength. This is because the two acrylamido buffers that bracket the desired pH have pKa values of about 4.6 (4-acrylamidobutyric acid) and about 6.2 (2-morpholinoethylacrylamide). The buffering capacity of a compound falls off logarithmically from the buffer's pKa. Thus, a fairly large amount of a base is required to titrate the pH of 4-acrylamidobutyric acid from 4.6 to 5.4, and a fairly large amount of an acid is required to titrate the pH of 2-morpholinoethylacrylamide from 6.2 to 5.4.

High percentages of acrylamido buffer disadvantageously lead to non-uniform electrical fields, physical instability of the gel, and increase cost. They also tend to disadvantageously increase the hydrophobicity of the gels, leading to protein retention. High percentages of acids and bases additionally cause, or at least increase the amount or rate of, breakdown of polyacrylamide, decreasing shelf life.

In contrast, embodiments of the IBDs of the present invention that include a gel that comprises a copolymerized dicarboxylic acid monomer are capable of having a desirably low "buffer ratio". By "buffer ratio" is meant the ratio (mol/mol) of buffer (e.g., pH conferring monomer plus titrant) to gel. In certain embodiments of the IBDs of the present invention, the buffer ratio may be less than about 15%, less than about 10%, less than about 5%, preferably less than about 1%, and most preferably less than about 0.1%.

By using less pH conferring monomer and titrant, dicarboxylic acid-containing gels of the present invention typically have a longer shelf-life compared to other gels and systems that do not utilize itaconic acid or other dicarboxylic acids.

In some embodiments, the IBD is stable when stored at 4° C. or at ambient temperature for at least 2 weeks to about 3, 4, 5, 6, 7, or 8 weeks, more preferably from about 1 month to about 2, 3, 4, 5, 6, 7, 8, 9, 10, 11 or 12 months, most preferably from about 1 year to about 2 or 3 years.

In certain embodiments, the dicarboxylic acid monomer may be copolymerized with an acrylamido buffer monomer, typically further copolymerized with acrylamide and an acrylamide crosslinker, such as N,N'-methylene-bis-acrylamide.

Although here described as a copolymerized component of IBDs of the present invention, dicarboxylic acids can be used as gel monomers in a variety of electrophoretic devices and methods, and are thus not limited to the compositions and methods disclosed herein.

The IBDs can usefully further include visible indicia, which may appear on either or both sides of the disk.

The indicia can be incorporated using, for example, the methods and compositions disclosed in co-pending and commonly owned U.S. Pat. No. 6,521,111 B1, published U.S. patent application US 2003/0038030 A1, and published PCT patent application WO 01/77655 A1. Such indicia include, without limitation, any one or more of the pH of the IBD, the manufacturer, the date of manufacture, the lot number, a trademark, and any other distinctive or useful mark. Exemplary trademarks include, without limitation, ZOOM®, Invitrogen™, NOVEX® and the Invitrogen design trademark (U.S. registration # 75912326).

Alternatively, the indicia can be printed directly on the disk using, e.g., ink jet printing approaches.

After polymerization, IBDs may be washed; washing may usefully reduce contaminants, such as unpolymerized monomers, buffer, or catalyst.

The IBDs may be washed, for example, in a low ionic strength solution buffered near neutrality. The wash solution can conveniently be based on the low ionic strength buffers described in U.S. Pat. Nos. 5,578,180, 5,922,185, 6,059,948, 6,096,182, 6,143,154, 6,162,338, the disclosures of which are incorporated herein by reference in their entirety.

For example, the wash solution can usefully comprise Bis-Tris ((2-hydroxyethyl)iminotris(hydroxymethyl)methane), Tricine, glycerol and/or sorbitol, EDTA, sodium azide, and SB-14 (3-(N,N-dimethylmyristylammonio)propanesulfonate), titrated to a neutral pH.

In addition or in the alternative, the IBDs can be washed with one or more reducing agents, such as those included in the running buffers described, e.g., in U.S. Pat. No. 5,578,180, the disclosure of which is incorporated herein by reference in its entirety. The reducing agent can, e.g., be sodium bisulfite.

IBDs that are particularly adapted for use in the device of the present invention will typically conform in shape to the lumen of the sample chamber, albeit with dimensions sufficiently larger than those of the chamber lumen as to permit the IBD to seat within the distal recess without passing into the lumen itself. In preferred embodiments, the amount by which the IBD exceeds the chamber lumen in size will be uniform around the entirety of the IBD circumference.

As described above, the lumen of the sample chambers of the present invention may usefully lack rotational symmetry. And as further described above, the lumen of the sample chambers of the present invention may advantageously lack symmetry across the horizontal plane. Accordingly, in certain embodiments, the IBDs of the present invention lack rotational symmetry, and in other embodiments additionally lack symmetry across the horizontal plane.

A variety of shapes comprising circular arcs of varying radii and separation distances can be designed that meet such criteria, including a variety of elliptical and pseudo-elliptical shapes, such as an ovoid shape.

Figure 11A:
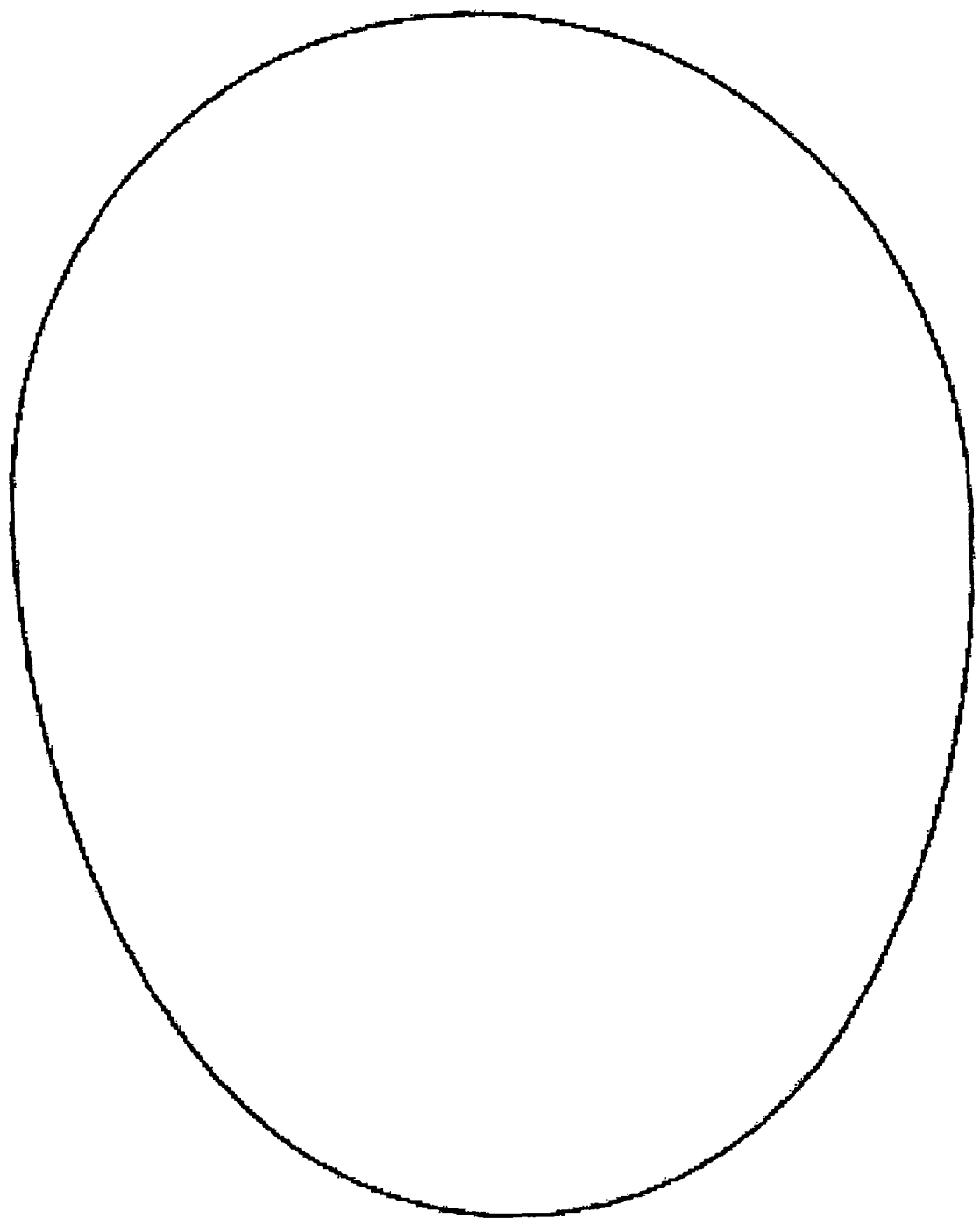
FIG. 11A is a front (or equivalently, back) orthogonal view of an exemplary immobilized buffer disk (IBD) of the present invention having an ovoid (pseudoelliptical) shape.

In one series of embodiments, the IBD of the present invention is ovoid, as illustrated in FIG. 11A: this pseudoelliptical shape advantageously lacks rotational symmetry and is non-symmetric across the horizontal plane.

Figure 11B:
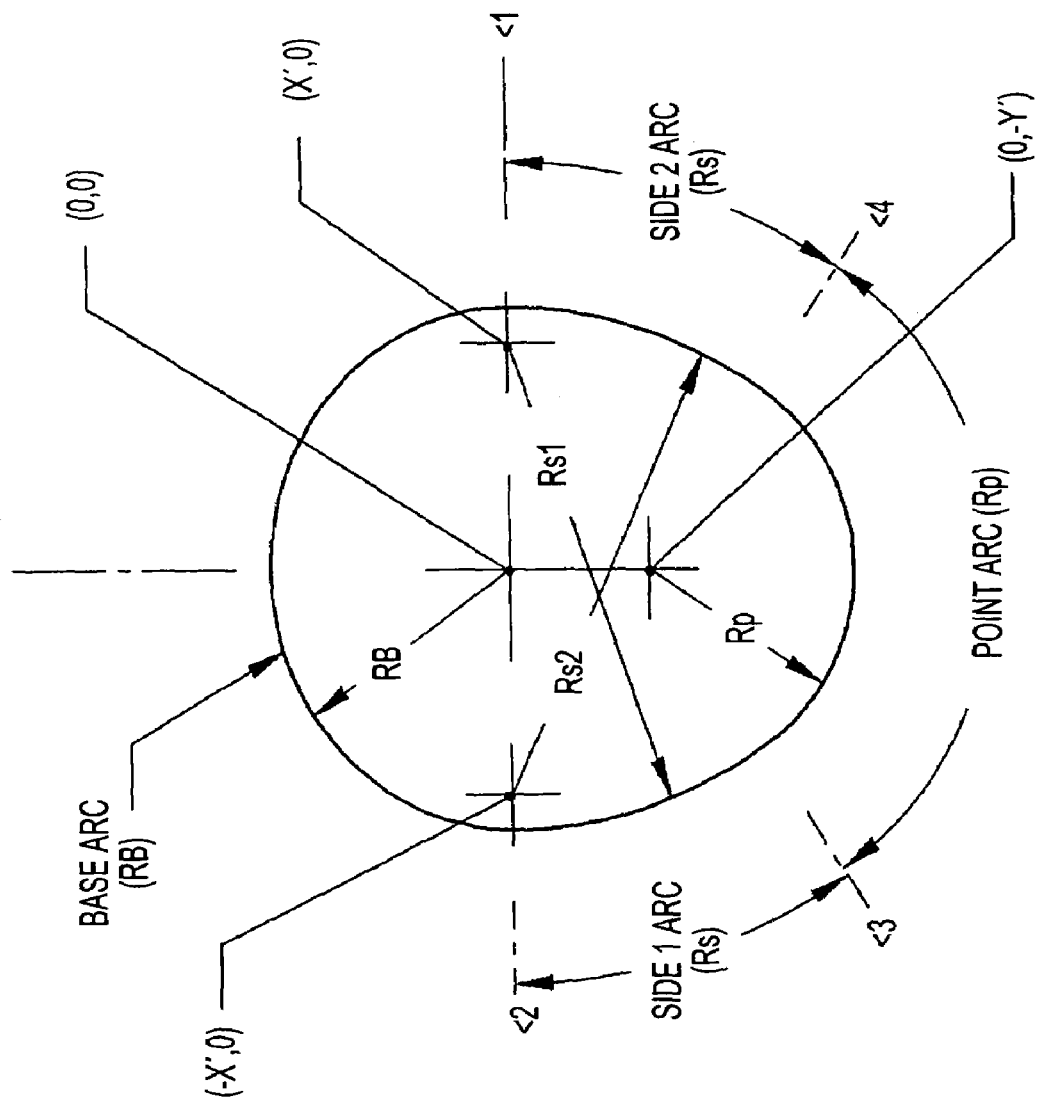
FIG. 11B gives an exemplary formula for designing a disk with such shape.

In one series of embodiments, the ovoid shape may be defined by the following general formulae, in which the arcs and angles are identified in FIG. 11B:

"Base" Arc:$x^2+y^2=R_B^2|_{\angle 1}^{\angle 2}$

"Side 1" Arc:$(x-x')^2+y^2=R_S^2|_{\angle 2}^{\angle 3}$

"Point" Arc:$x^2+[y-(-y')]^2=R_P^2|_{\angle 3}^{\angle 4}$

"Side 2" Arc:$[x-(-x')]^2+y^2=R_S^2|_{\angle 4}^{\angle 1}$ (2)

Where $R_{S1}=R_{S2}$
and $|-x'|=x'$
and $R_P<R_B<R_S$

In a particular one of these embodiments, for example, $R_{S1}=R_{S2}=11.89$ mm; $R_P=5.26$ mm; $R_B=6.37$ mm; <1=0°; <2=180°; <3=213.76°; <4=326.24°; X'=|–X'|=5.52 mm; and (0, —Y')=(0, –3.68 mm). This shape and size are suitable for use with a chamber having a lumenal volume of about 650-750 μl.

Variations from this exemplary shape are within the scope of this invention. For example, the separation (y) of centerlines between the "base" and "point" arcs (dimension Y' in the figures) may be as low as about 3.0 mm, and as high as about 25.4 mm. That is, the separation can be any value, including by way of non-limiting example, about 3, about 4, about 5, about 6, about 7, about 8, about 9, about 10, about 11, about 12, about 13, about 14, about 15, about 16, about 17, about 18, about 19, about 20, about 21, about 22, about 23, about 24 or about 25 mm. Fractions and sub-fractions of the preceding separation values can also be used. For example, in the case of separations between about 3 to about 4 mm, the separation can be about 3.0, about 3.1, about 3.2, about 3.3, about 3.4, about 3.5, about 3.6, about 3.7, about 3.8, about 3.9 or about 4.0 mm. As a further example, in the case of separations between about 3.0 to about 3.1 mm, the separation can be about 3.00, about 3.01, about 3.02, about 3.03, about 3.04, about 3.05, about 3.06, about 3.07, about 3.08, about 3.09 or about 3.10 mm.

Variations from the exemplary size are also within the scope of this invention.

For example, the size can be scaled up or down at any factor suitable for any chamber lumenal volume. By way of non-limiting example, for volumes between 1,500 and 500 μl, a disk designed for a 750 μl chamber lumenal volume could be scaled up or down by a factor of 5× up to 0.3×, respectively.

Additional desirable dimensional and shape criteria optionally include: (1) minimization of the size of the disk; (2) minimization of the area of the disk outside of the chamber lumen; (3) provision of a full and adequate seal between adjacent chambers; (4) maintenance of uniformity of an electrical field that mobilizes molecules through the disk; and (5) maintenance of a specific orientation between adjacent seals and surfaces.

Kits

In another aspect, the invention provides kits for performing solution phase isoelectric focusing using the device and components of the present invention.

In one series of embodiments, the kit provides components that can be assembled into the device of the present invention. The kit components may be sufficient to assemble a complete device, optionally with spare parts, or may instead include only a subset of device components.

The kit may, for example, include one or more of a spill trough with integral cathode buffer chamber, a loading tube with integral anode buffer chamber, lid with electrodes, and chamber stack components. The chamber stack components may include O-rings, sample chambers, sample chamber fill port cap seals, spacers and/or IBDs, cathode end piece, and anode end piece. The kit may also include one or more of end screw cap, and electrode plugs.

In another series of embodiments, the kit provides only disposable items, such as spacers and/or IBDs.

For example, the kits may include only IBDs, for example a plurality of IBDs each having the same fixed pH, such as pH 3.0, 4.6, 5.4, 6.2, 7.0, and 10.0. Each of the plurality of disks may be separately packaged, or the disks may be physically segregated within a common package.

For example, in one embodiment, a plurality of IBDS, such as 2, 3, 4, even 5, 6, 7, 8, 9, or 10 or more IBDS, each having the same fixed pH, are physically segregated from one another within a single blister pack or strip, such as those described in U.S. Pat. No. 4,691,820.

A blister pack, strip or package typically consists of two pieces: a base and a cover. The base is an injection-molded plastic that typically has a bowl-shaped, or rectangular-shaped, recess for receiving and holding an IBD. The cover is a laminate material that typically consists of a laminate of an aluminum foil and polypropylene. The sealing of the cover layer to the base portion, or its flange, can be carried out by the action of heat or ultrasound, or by means of some other suitable bonding process. Once sealed, a series of individual sealed pockets ("blisters") is formed, each one of which comprises an individual IBD.

Typically, each blister also comprises a hydrating and/or buffering solution to prevent drying of the IBD and to maintain the IBD ready for use. The solution is conveniently a low ionic strength solution buffered near neutrality, typically further comprising one or more agents to maintain the suppleness of the support and one or more preservatives, such as sodium azide and/or a chelating agent, such as EDTA. The solution can conveniently be based on the low ionic strength buffers described in U.S. Pat. Nos. 5,578,180, 5,922,185, 6,059,948, 6,096,182, 6,143,154, 6,162,338, the disclosures of which are incorporated herein by reference in their entirety.

For example, the solution can usefully comprise BisTris ((2-hydroxyethyl)iminotris(hydroxymethyl)methane), Tricine, glycerol and/or sorbitol, EDTA, sodium azide, and SB-14 (3-(N,N-dimethylmyristylammonio)propane-sulfonate), titrated to a neutral pH.

Typically, the amount of solution in a given blister is between 0.8 to 5 ml, with most between 1 and 3 ml, typically about 1 ml.

In another embodiment, each "blister" of a single blister pack or strip comprises a single IBD, each of the IBDs in the pack or strip having a different fixed pH, so that one strip contains all of the requisite IBDs for operation of the device. For example, a blister pack can contain a series of IBDs having pH values of 3.0, 4.6, 5.4, 6.2, 7.0 and 10.0.

In yet other embodiments, the kits may include a plurality of such common pH IBDS, with the plurality including IBDs of a plurality of pHs, permitting multiple operations of the device of the present invention.

In other embodiments, the kits may include, either separately or in conjunction with any of the kits above-described, any one or more reagents useful in solution phase isoelectric focusing, such as carrier ampholytes, anode buffer (e.g., as a 50× concentrate), and cathode buffer (e.g., for pH 3-10, at 10× concentrate). The kits may also include one or more reagents for solubilizing and/or denaturing proteins, such as urea, thiourea, and CHAPS (3-[(cholamidopropyl)dimethylammonio]-propanesulfonate).

The kits of the present invention may further comprise one or more sets of instruction, one or more protein standards, and/or one or more control samples.

Yet other kits may commonly package a plurality of IBDS, with various fixed pHs, with one or more immobilized pH gradient (IPG) strips having pH range suitable for further analysis of fractions bracketed by the included IBD pHs.

Methods

The device and immobilized buffer disks of the present invention can readily be used for solution phase isoelectric focusing (IEF), particularly for solution phase isoelectric focusing prefractionation of samples prior to further analysis, such as by 2D PAGE.

In a typical embodiment of the methods of the present invention, protein samples are prepared in sample buffer; the sample chambers and appropriate IBDs are assembled within the loading tube; the samples are loaded into the sample chambers; the sample chambers are capped with cap seals; anode buffer is added to the anode reservoir and cathode buffer is added to the cathode buffer chamber; fractionation is performed; cap seals are removed and sample fractions retrieved; and the fractions then used for downstream analytical applications.

As would be understood, the steps as listed above, and their order, are exemplary.

In a first step of this exemplary method, protein samples are prepared in sample buffer. Preparation of samples for isoelectric focusing is known in the art. See, e.g., Rabilloud, Proteome Research: Two Dimensional Gel Electrophoresis and Identification Tools, Springer Verlag (2000) (ISBN: 3540657924) and Rabilloud, *Methods Mol. Biol.* 112:9-19 (1999), the disclosures of which are incorporated herein by reference in their entireties.

As is well known, the major objectives of sample preparation are to completely solubilize the proteins, denature the proteins, reduce disulfide bonds, prevent protein modification, and maintain the proteins in solution during solution phase IEF. Accordingly, the sample buffer typically contains: urea, for denaturation and solubilization, and/or thiourea; detergent, such as non-ionic or zwitterionic detergents, for solubilization, such as CHAPS, NP-40, CAPSO, and sulfobetaines; DTT or DTE (dithioerythritol), as a reducing agent; and ampholytes, which help solubilize the proteins and maintain the pH gradient. Ampholytes are typically used at concentrations of about 0.2-2% (v/v); higher concentrations require longer focusing times.

Optionally, but preferably, the sample proteins can be reduced and alkylated by treating with DTT followed by alkylation in the presence of N,N-dimethylacrylamide (DMA). Also optionally, particulate material can be removed by high-speed centrifugation to reduce the chance of clogging the IBDs.

In embodiments of the device of the present invention in which sample chambers have volumes of about 700 μl, samples are typically then diluted to about 0.6 mg protein/ml.

In the next step, the chambers are assembled as described herein above.

In one exemplary assembly method, O-rings are placed on the proximal projections and cap seals within the fill ports of each of 7 exemplary sample chambers. The loading tube is held vertically and the anode end piece inserted therein. A first (most proximal) chamber is then inserted into the loading tube with its cap seal projecting through the loading tube channel. A pH 3.0 IBD is placed in the first chamber's distal recess. A second chamber is then inserted into the loading tube, and a pH 4.6 IBD placed in its distal recess. The process is repeated with IBDs having pH 5.4, 6.2, 7.0 and 10.0. A final ($7^{th}$) sample chamber is inserted, followed by the cathode end piece. The end screw is screwed onto the loading tube to effect sealing engagement among the sample chambers within the loading tube.

As is described in greater detail above, the number of chambers, and the order of IBDs therebetween, is not limited to this exemplary embodiment.

For example, with 7 chambers, the device may be assembled with fewer than 6 IBDs, using spacers in lieu of one or more IBDs.

For example, for fractionating in the pH 4-5 range, the following exemplary chamber stack order may be used (from proximal to distal): anode end piece, chamber, pH 3.0 IBD, chamber, spacer, chamber, pH 4.6 IBD, chamber, pH 5.4 IBD, chamber, spacer, chamber, pH 10.0 IBD, chamber, cathode end piece.

For fractionating in the pH 5-6 range, the following exemplary chamber stack order may be used (from proximal to distal): anode end piece, chamber, pH 3.0 IBD, chamber, spacer, chamber, pH 5.4 IBD, chamber, pH 6.2 IBD, chamber, spacer, chamber pH 10.0 IBD, chamber, cathode end piece.

For fractionating in the pH 5-7 range, the following exemplary chamber stack order may be used (from proximal to distal): anode end piece, chamber, pH 3.0 IBD, chamber, spacer, chamber, pH 5.4 IBD, chamber, pH 7.0 IBD, chamber, spacer, chamber, pH 10.0 IBD, chamber, cathode end piece.

For fractionating in the pH 3-4 range, the following exemplary chamber stack order may be used (from proximal to distal): anode end piece, chamber, spacer, chamber, pH 3.0 IBD, chamber, pH 4.6 IBD, chamber, spacer, chamber, spacer, chamber, pH 10.0 IBD, chamber, cathode end piece.

Next, the loading tube is inserted into the spill trough so that the end screw sealingly engages the cathode buffer chamber.

Anode buffer and cathode buffer chambers are then filled with respective buffers.

Next, the samples are loaded into the sample chambers: cap seals are removed, and sample added to each nonblank chamber (i.e., chamber partitioned on both sides by an IBD). In one exemplary embodiment, 670 μl is added to each nonblank chamber. Cap seals are reinserted into the chamber fill ports.

The lid is then engaged to the spill trough, and the electrodes attached to a power supply.

Exemplary electrical parameters are 100 V for 20 minutes, 200 V for 80 minutes, and 600 V for 80 minutes. If the power supply has a current and power limiting capability, the current limit may usefully be set at 2 mA and the power limit at 2 W.

If current is flowing through the system, bromophenol blue included in the sample migrates towards the anode reservoir, usefully coloring it yellow as a visual check.

Following electrophoresis, the power supply is turned off, the lid removed, the cap seals removed and sample fractions retrieved. The fractions may usefully be removed using, e.g., a 1 ml pipette tip on a pipettor. The fractions may usefully be transferred to separate microcentrifuge tubes. To recover all of the fraction, the chamber may be washed with a wash buffer (e.g., sample buffer without any inhibitors).

The fractions may then be used for downstream analytical applications.

For example, after suitable dilution and/or desalting, the fractions may be subjected to one dimensional electrophoresis using SDS-PAGE, or 2D liquid chromatography/mass spectrometry (or 2D LC/MS/MS) analysis.

Alternatively, the fractions may be applied directly to immobilized pH gradient (IPG) strips for 2D PAGE analysis. Typically, neither buffer exchange nor further sample processing is required prior to IPG IEF, since the fractionated sample is in the same buffer required for first dimension IEF using IPG strips.

In one approach, fractions are applied to IPG strips which have pH range about 0.1 pH unit wider than the nominal pH range of the solution phase IEF fraction.

The device and methods of the present invention permit fractionation of complex samples by solution phase isoelectric focusing. By so doing, the device and methods of the present invention allow the loading of increased amounts of protein in downstream applications, such as 2D-PAGE, reduce sample complexity, result in high resolution and identification of low abundance proteins, increase the dynamic range of detection by increasing the concentration of protein species, and reduce precipitation/aggregation artifacts of samples at high protein loads during 2D gel electrophoresis.

Additional Applications

Although features and aspects of the device of the present invention are illustrated above in embodiments of solution IEF devices, one of skill in the art would recognize that many aspects described would be advantageous in the field of electrophoresis generally.

For example, the use of a loading tube sealed at the end with an end cap, such as a screw cap, that provides a circumferentially uniform, axially-directed pressure, would also be useful in sealing chambers in an electroelution device, or in a tube gel electrophoresis device.

As another example, the anode and cathode plugs described above would be useful in any electrophoresis device. The ease of cleaning and replacement, the sturdiness, and the ability to use very thin fragile wire would be advantageous in all forms of electrophoresis.

As yet a further example, one of skill in the art would recognize that the tapered fill port and cap seal arrangement described above would be generally useful in any device in which a chamber is desirably to be sealed without trapping air. Any device in which air bubbles disrupt an electric field, such as electroelution chambers, free solution electrophoresis devices, and others would benefit from a sealing mechanism that helps exclude air.

The following examples are offered by way of illustration, not by way of limitation.

EXAMPLE 1

Fractionation of Rat Liver Lysate

Rat liver tissue is lysed by sonication at a final concentration of 5% (w/v) in 7M urea, 2M thiourea, 4% CHAPS (collectively, "UTC") and protease inhibitors. After reduction, alkylation, centrifugation, and determination of the protein concentration of the supernatant fraction, samples are diluted to 0.6 mg/ml protein in UTC containing 1% ZOOM® ampholytes, pH 3-10 (Invitrogen Corp., Carlsbad, Calif., USA), 20 mM DTT, and a trace of bromophenol blue dye.

An aliquot of 3.35 ml is distributed equally into five central sample chambers of seven total chambers, each with capacity of about 670 µl, designed and assembled according to the device of the present invention. The five chambers are partitioned from one another by IBDs having pH 3.0, 4.6, 5.4, 6.2, 7.0, and 10.0.

After fractionation for 3 hours, the resulting fractions are collected and a 155 µl aliquot of each fraction is loaded onto a separate ZOOM® IPG strips (Invitrogen Corp., Carlsbad, Calif., USA). As a control, an aliquot of 155 µl of unfractionated sample (92 µg unfractionated rat liver lysate proteins) is loaded directly onto a ZOOM® 3-10 NL Strip (Invitrogen Corp., Carlsbad, Calif., USA).

The ZOOM® Strips are allowed to rehydrate with the applied samples overnight, and then focused in a ZOOM® IPGRunner™ System (Invitrogen Corp., Carlsbad, Calif., USA). The focused ZOOM strips are then applied to NuPAGE® Novex 4-12% Bis-Tris ZOOM® gels. The resulting 2DE gels are stained with SimplyBlue™ SafeStain (Invitrogen Corp., Carlsbad, Calif., USA) and scanned.

FIGS. 12A-12F are scanned images of the resulting 2D gels.

The pH range of the immobilized pH gradient (IPG) strip is shown immediately beneath each gel image.

Figure 12:
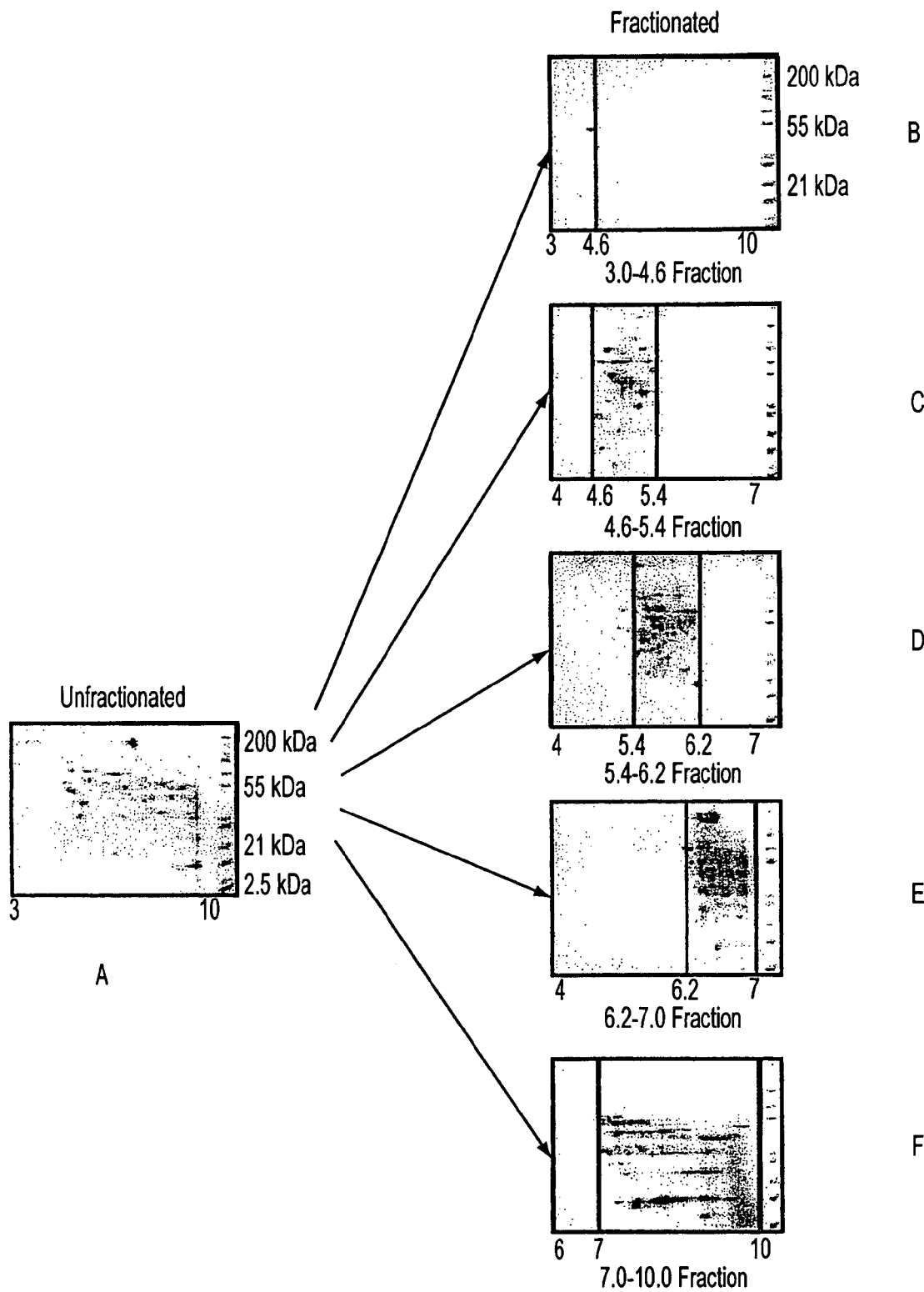
FIGS. 12A-12F are scanned images of 2D gels—obtained by immobilized pH gradient (IPG) isoelectric focusing, using either pH 3-10 strips, pH 4-7 strips, or pH 6-10 strips, as indicated immediately below each gel image, followed by SDS-PAGE—demonstrating the effects of prefractionating a rat liver tissue lysate into five separate fractions using a device, components, and methods of the present invention.

FIG. 12A is obtained with unfractionated lysate. Each of FIGS. 12B-12F is obtained using a fraction from a different one of the device sample chambers; the pH range of the device sample chamber is shown in large type below the IPG strip pH range.

The results show that the device of the present invention can efficiently separate a complex proteome, such as rat liver tissue, into five well defined fractions based on pH. The fractionation reduces the sample's complexity while increasing the concentration of the fractionated proteins.

EXAMPLE 2

Improvement in Detection of Low Abundance Proteins

Rat liver lysate is prepared and fractionated in a device of the present invention, essentially according to Example 1.

Separate 155 µl aliquots of the pH 4.6-5.4 fraction are loaded respectively on a pH 4.5-5.5 narrow range ZOOM® IPG strip (Invitrogen Corp., Carlsbad, Calif., USA) and a pH 4-7 ZOOM® IPG strip (Invitrogen Corp., Carlsbad, Calif., USA) and allowed to rehydrate overnight. The applied proteins are then focused using the ZOOM® IPGRunner™ System (Invitrogen Corp., Carlsbad, Calif., USA). The focused ZOOM® Strips are separately applied to NuPAGE® Novex 4-12% Bis-Tris ZOOM gels. The resulting 2DE gels are stained with SimplyBlue™ SafeStain and scanned.

Unfractionated rat liver lysate is analogously applied to a pH 4.5-5.5 narrow range ZOOM® IPG strip (Invitrogen Corp., Carlsbad, Calif., USA) as a control.

Figure 13:
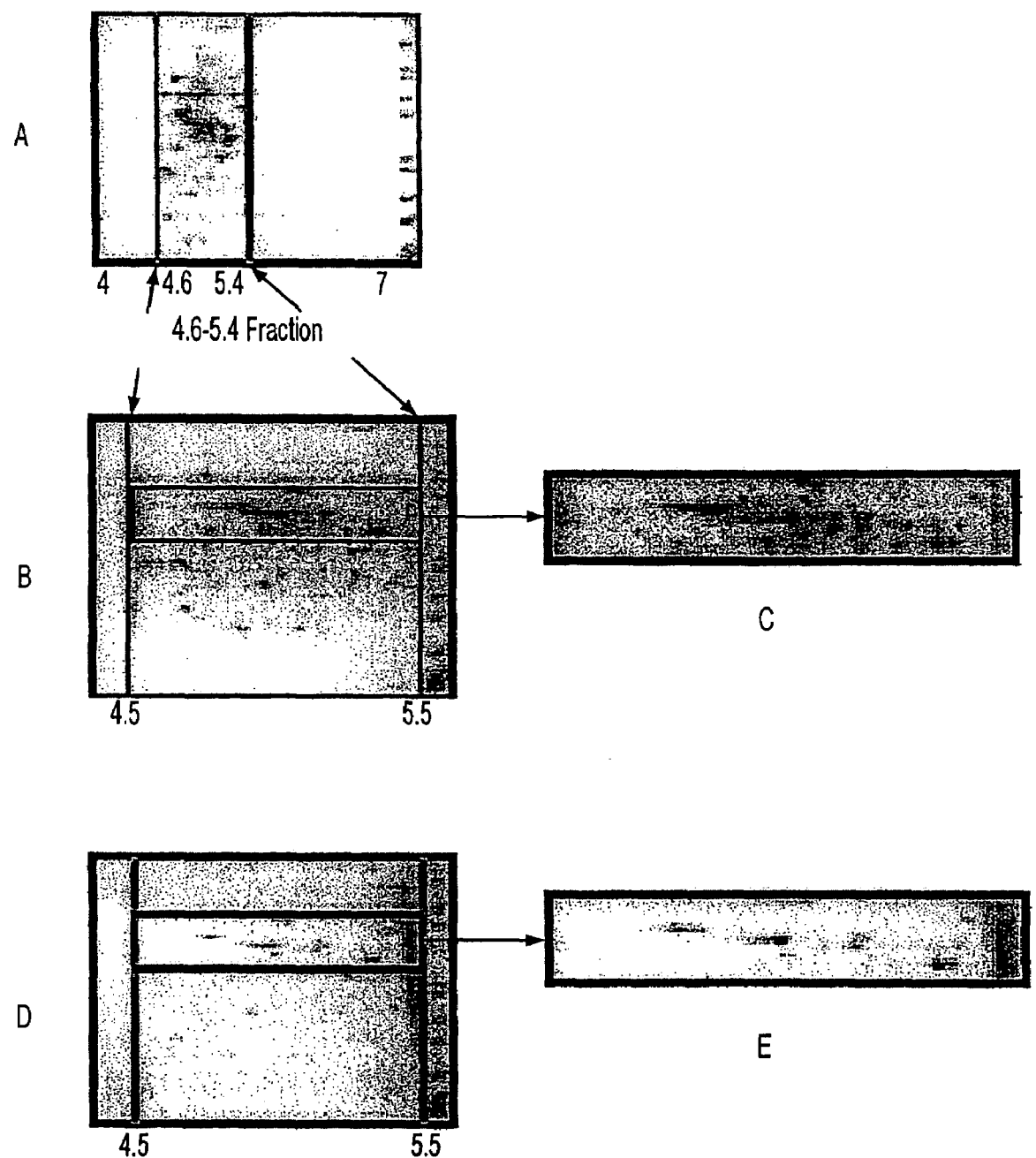
FIGS. 13A-13E are scanned images of 2D gels.

FIG. 13A shows the solution phase fraction run on a pH 4-7 IPG strip, demonstrating that prefractionation in the device of the present invention yields a fraction with clearly defined pI range.

FIG. 13B is an equivalent solution phase pH 4.6-5.4 fraction run on a pH 4.5-5.5 narrow range narrow range IPG strip. FIG. 13C shows an enlargement of the indicated region of the gel shown in FIG. 13B. By comparison, FIG. 13D is obtained from unfractionated rat liver lysate using a pH 4.5-5.5 IPG strip, with FIG. 13E showing an enlargement of the indicated region of the gel shown in FIG. 13D.

Comparison of FIGS. 13C and 13E demonstrate that prefractionation using the device of the present invention improves the ability to detect low abundance proteins.

All patents, patent publications, and other published references mentioned herein are hereby incorporated by reference in their entirety as if each had been individually and specifically incorporated by reference herein.

Examples are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such deviations and modifications that fall within the true spirit and scope of the invention.

The invention claimed is:

1. A device for solution phase electrophoretic separation of analytes within a sample, comprising:
   an anode within an anode buffer chamber;
   a cathode within a cathode buffer chamber;
   a chamber stack disposed between said anode and said cathode; and
   chamber stacking means external to said chamber stack;
   wherein said chamber stack comprises a plurality of detachably mated sample chambers having lumens aligned along the electrical axis between said anode and cathode, the lumens of said coaxially aligned sample chambers being collectively capable of defining an electrically conductive fluid column therethrough;
   wherein said chamber stack further comprises a plurality of junctional partitions, each of said partitions positioned at a different one of the junctions between adjacent sample chambers, said partitions being permeable to ions and to at least a plurality of the analytes in said sample;
   wherein said chamber stacking means includes a loading tube and a removable end cap that engages said loading tube to secure said chamber stack, wherein said end cap comprises a lumen that permits fluid communication between the interior of said chamber stack and one of said anode buffer chamber and said cathode buffer chamber.

2. The device of claim 1, wherein the lumen of each of said sample chambers is rotationally nonsymmetric within the vertical plane orthogonal to the electrical axis.

3. The device of claim 1, wherein the lumen of each of said sample chambers is nonsymmetric across the horizontal plane through the midpoint of the lumen.

4. The device of claim 3, wherein the lumen of each of said sample chambers is ovoid within the vertical plane orthogonal to the electrical axis.

5. The device of claim 4, wherein the lumen of each of said sample chambers has a more acute radius of curvature at the bottom than at the top.

6. The device of claim 1, wherein the lumen of each of said sample chambers has a volume or less than about 2 ml.

7. The device of claim 6, wherein-the lumen of each of said sample chambers has a volume of less than about 1.5 ml.

8. The device of claim 7, wherein the lumen of each of said sample chambers has a volume of less than about 1.0 ml.

9. The device of claim 8, wherein the lumen of each of said sample chambers has a volume of less than about 750 microliters.

10. The device of claim 9, wherein the lumen of each of said sample chambers has a volume of about 600-700 microliters.

11. The device of claim 1, wherein each sample chamber of said plurality of sample chambers further comprises at least one port, said at least one port capable of fluidly connecting the lumen of the sample chamber with the exterior of said chamber when said chamber is mated within the chamber stack.

12. The device of claim 11, wherein the lumen of said sample chamber is ovoid with a more acute radius of curvature at the bottom than at the top, and at least one of said sample chamber ports is at the top of each said chamber.

13. The device of claim 12, wherein said at least one port is inwardly tapered.

14. The device of claim 1, wherein said sample chambers are capable of mating solely by application of axially directed force.

15. The device of claim 14, wherein said mated chambers are incapable of interchamber rotation.

16. The device of claim 15, wherein the mating of said chambers positions all said chamber ports upward.

17. The device of claim 1, wherein each said partition has the shape of a sample chamber lumen.

18. The device of claim 17, wherein each said partition has a rotationally nonsymmetric pseudoelliptical shape.

19. The device of claim 1, wherein at least a plurality of said partitions have a fixed pH.

20. The device of claim 19, wherein each of said plurality has a different fixed pH.

21. The device of claim 19, wherein each said partition comprises a copolymer of acrylamide, an acrylamide crosslinker, and at least one species of pH-conferring monomer.

22. The device of claim 21, wherein said at least one species of pH-conferring monomer is an acrylamido buffer.

23. The device of claim 21, wherein said at least one species of pH-conferring monomer is a dicarboxylic acid.

24. The device of claim 23, wherein said dicarboxylic acid is itaconic acid.

25. The device of claim 1, wherein said chamber stacking means is capable of applying a circumferentially uniform, axially directed compressive force upon said chamber stack.

26. The device of claim 1, wherein said loading tube and said removable end cap are both at least partially threaded, and the thread of said end cap is capable of engaging the thread of said stacking tube.

27. The device of claim 26, wherein said loading tube thread is external to said tube and said end cap thread is internal to said cap.

28. The device of claim 1, wherein said loading tube has an axially oriented channel that extends entirely through a wall of said tube.

29. The device of claim 28, wherein the transaxial dimensions of said channel closely accommodate the external projection of cap seals, said cap seals sealingly insertable into said sample chamber ports.

30. The device of claim 1, wherein the lumen of said end cap permits fluid communication between said anode buffer chamber and the interior of said chamber stack.

* * * * *